United States Patent
Doi et al.

(10) Patent No.: US 8,531,479 B2
(45) Date of Patent: Sep. 10, 2013

(54) ENDOSCOPE APPARATUS AND PROGRAM

(75) Inventors: Takahiro Doi, Tokyo (JP); Saichi Sato, Sagamihara (JP); Masayoshi Yokota, Tokyo (JP); Kiyotomi Ogawa, Tokyo (JP); Sumito Nakano, Tokyo (JP); Yuusuke Kuwa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1125 days.

(21) Appl. No.: 12/483,459

(22) Filed: Jun. 12, 2009

(65) Prior Publication Data

US 2010/0317920 A1    Dec. 16, 2010

(51) Int. Cl.
*G09G 5/00*    (2006.01)

(52) U.S. Cl.
USPC ............ 345/619; 345/581; 345/629; 345/660; 345/684; 345/688

(58) Field of Classification Search
None
See application file for complete search history.

(56) References Cited

U.S. PATENT DOCUMENTS

| | | |
|---|---|---|
| 2007/0165306 A1 | 7/2007 | Bendall et al. |
| 2009/0167847 A1* | 7/2009 | Doi ................................. 348/65 |

FOREIGN PATENT DOCUMENTS

| | | | |
|---|---|---|---|
| JP | 4-332523 A | | 11/1992 |
| JP | 10-133639 A | | 5/1998 |
| JP | 10133639 A | * | 5/1998 |
| JP | 2009-086553 | | 4/2009 |

\* cited by examiner

*Primary Examiner* — Kee M Tung
*Assistant Examiner* — Jwalant Amin
(74) *Attorney, Agent, or Firm* — Holtz, Holtz, Goodman & Chick, PC

(57) ABSTRACT

An endoscope apparatus includes: an imaging portion imaging a subject to generate image data; a designation portion designating a position in an image based on the image data; an image processing portion processing the image data such that an enlarged image obtained by enlarging an image in a second region including the designated position overlaps a first region including the designated position designated by the designation portion; a display portion displaying the enlarged image and the image of the subject based on the image data processed by the image processing portion and displays a cursor at the designated position on the enlarged image; and a measurement processing portion performing measurement on the basis of a measurement position indicated by the cursor by using the image data generated by the imaging portion. The enlarged image displayed on the display portion moves according to movement of the cursor.

8 Claims, 17 Drawing Sheets

ENDOSCOPE APPARATUS AND PROGRAM

BACKGROUND OF THE INVENTION

1. Field of the Invention

The present invention relates to an endoscope apparatus, which performs measurement on the basis of image data obtained by imaging a subject, and a program.

2. Description of Related Art

Industrial endoscope apparatuses are used to observe or check inside damage, corrosion, and the like of a boiler, a turbine, an engine, a pipe, and the like. Moreover, among the endoscope apparatuses, there is an endoscope apparatus having a function of measuring the lengths area and the like using the principle of triangulation on the basis of a measurement point designated on an image imaged by the endoscope. This endoscope apparatus has a plurality of kinds of optical adapters prepared to observe and check various objects, and a tip portion of the endoscope apparatus can be replaced.

An example of such an optical adapter includes a stereo optical adapter capable of imaging two subject images of the same subject. Using the stereo optical adapters the length, area and the like of the subject can be measured by calculating the three-dimensional spatial coordinates of the subject using the principle of triangulation on the basis of the coordinates of left and right optical system distance calculating points when the subject image is captured by the left and right optical systems.

FIG. 24 shows a display screen of an endoscope apparatus. A left image 901L and a right image 901R corresponding to left and right subject images captured by a stereo optical adapter are displayed on a display screen 900 shown in FIG. 24. In addition, cursors 902a and 902b for designating measurement points indicating measurement positions are displayed on the display screen 900. The user can move the cursors 902a and 902b within the display screen 900 by inputting the movement instruction of the cursor 902a to the endoscope apparatus.

The display position of the cursor 902a is set on the basis of the instruction that the user inputs to the endoscope apparatus. When the cursor 902a is set in the left image 901L, the matching process of calculating the position of a corresponding point on the right image 901R corresponding to the display position of the cursor 902a is executed. The position of the corresponding point becomes the display position of the cursor 902b. In addition, an image in which a surrounding region of the cursor 902a is enlarged is displayed in a zoom window 903a, and an image in which a surrounding region of the cursor 902b is enlarged is displayed in a zoom window 903b. Japanese Unexamined Patent Publication First Publication No. 2009-86553 discloses an endoscope apparatus which displays the same zoom windows as described above.

SUMMARY OF THE INVENTION

An endoscope apparatus according to an aspect of the invention includes: an imaging portion that images a subject to generate image data; a designation portion that designates a position in an image based on the image data; an image processing portion that processes the image data such that an enlarged image obtained by enlarging an image in a second region including the designated position overlaps a first region including the designated position designated by the designation portion; a display portion that displays the enlarged image and the image of the subject based on the image data processed by the image processing portion and displays a cursor at the designated position on the enlarged image; and a measurement processing portion that performs measurement on the basis of a measurement position indicated by the cursor by using the image data generated by the imaging portion.

The enlarged image displayed on the display portion moves according to the movement of the cursor. A program that controls an operation of an endoscope apparatus according to an aspect of the invention causes the endoscope apparatus to execute: a step of imaging a subject to generate image data; a step of designating a position in an image based on the image data; a step of processing the image data such that an enlarged image obtained by enlarging an image in a second region including the designated position overlaps a first region including the designated position that has been designated; a step of displaying the enlarged image and the image of the subject based on the image data processed by the image processing portion and displaying a cursor at the designated position on the enlarged image; and performing measurement on the basis of a measurement position indicated by the cursor by using the image data generated by the imaging portion. The enlarged image displayed on the display portion moves according to movement of the cursor.

DETAILED DESCRIPTION OF THE INVENTION

Figure 1:
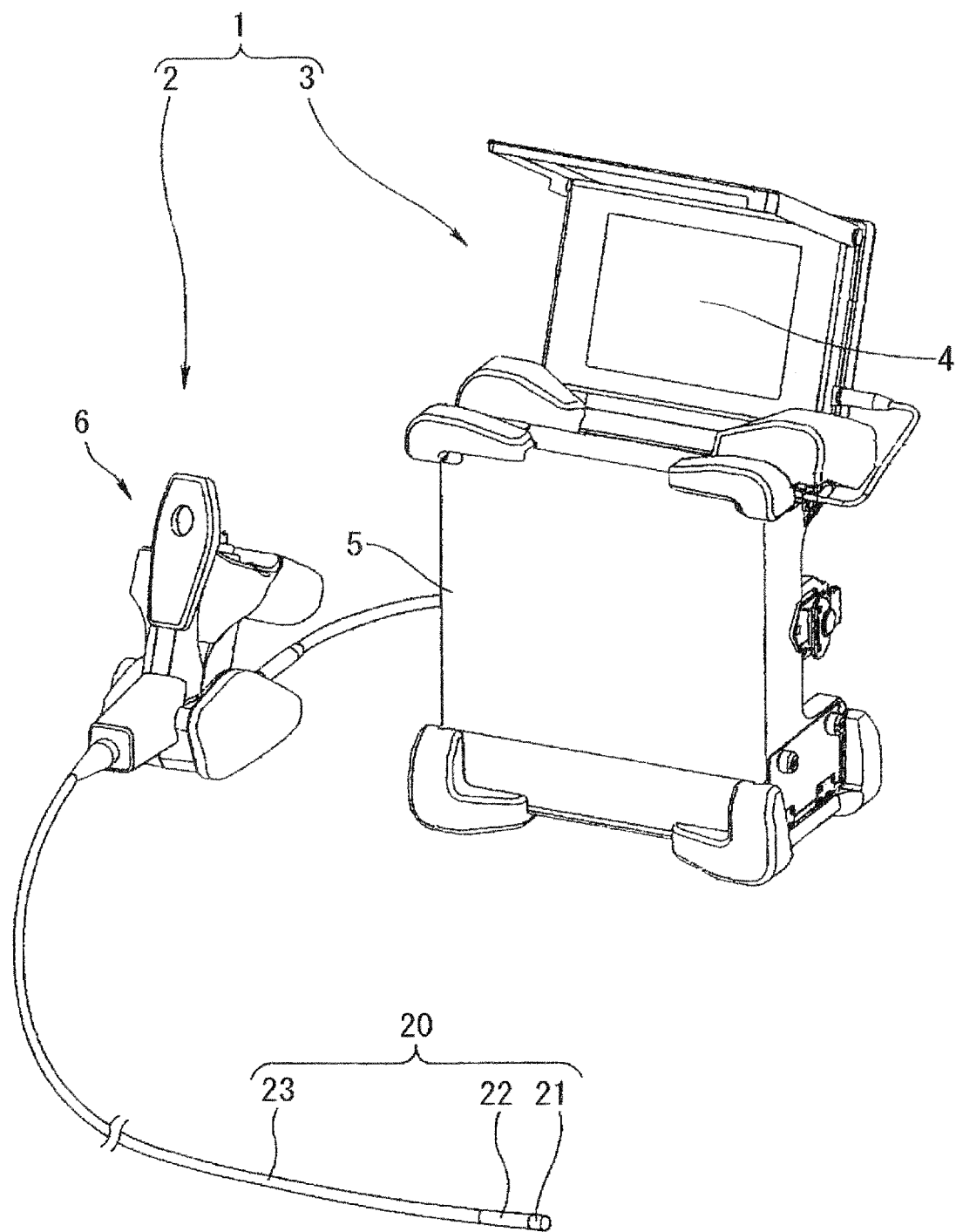
FIG. 1 is a perspective view illustrating the entire configuration of an endoscope apparatus according to an embodiment of the invention.

Hereinafter, embodiments of the invention will be described with reference to the drawings. FIG. 1 shows the configuration of an endoscope apparatus according to an embodiment of the invention. As shown in FIG. 1, an endoscope apparatus 1 includes an endoscope 2 and an apparatus body 3 connected to the endoscope 2. The endoscope 2 includes a long and thin inserted portion 20 and an operating portion 6 for performing an operation required in executing various kinds of operation controls of the entire apparatus. The apparatus body 3 includes a monitor 4 (liquid crystal display), which is a display device that displays an image of a subject imaged by the endoscope 2, contents of an operation control (for example, a processing menu), and the like, and a housing 5 having a control unit 10 (refer to FIG. 2).

The inserted portion 20 is formed by connecting a hard tip portion 21, a bent portion 22 which can be bent, for example, in the upper, lower, left, and right directions, and a flexible tube portion 23 with the flexibility sequentially from the tip side. Various kinds of optic adapters, such as a stereo optical adapter having two observation fields of view or a normal observation optical adapter having one observation field of view, are freely attached to the tip portion 21 or detached from the tip portion 21. In the present embodiment, when performing measurement, left and right images which are a pair of subject images on the left and right sides are imaged by the stereo optical adapter capable of imaging two subject images of the same subject.

Figure 2:
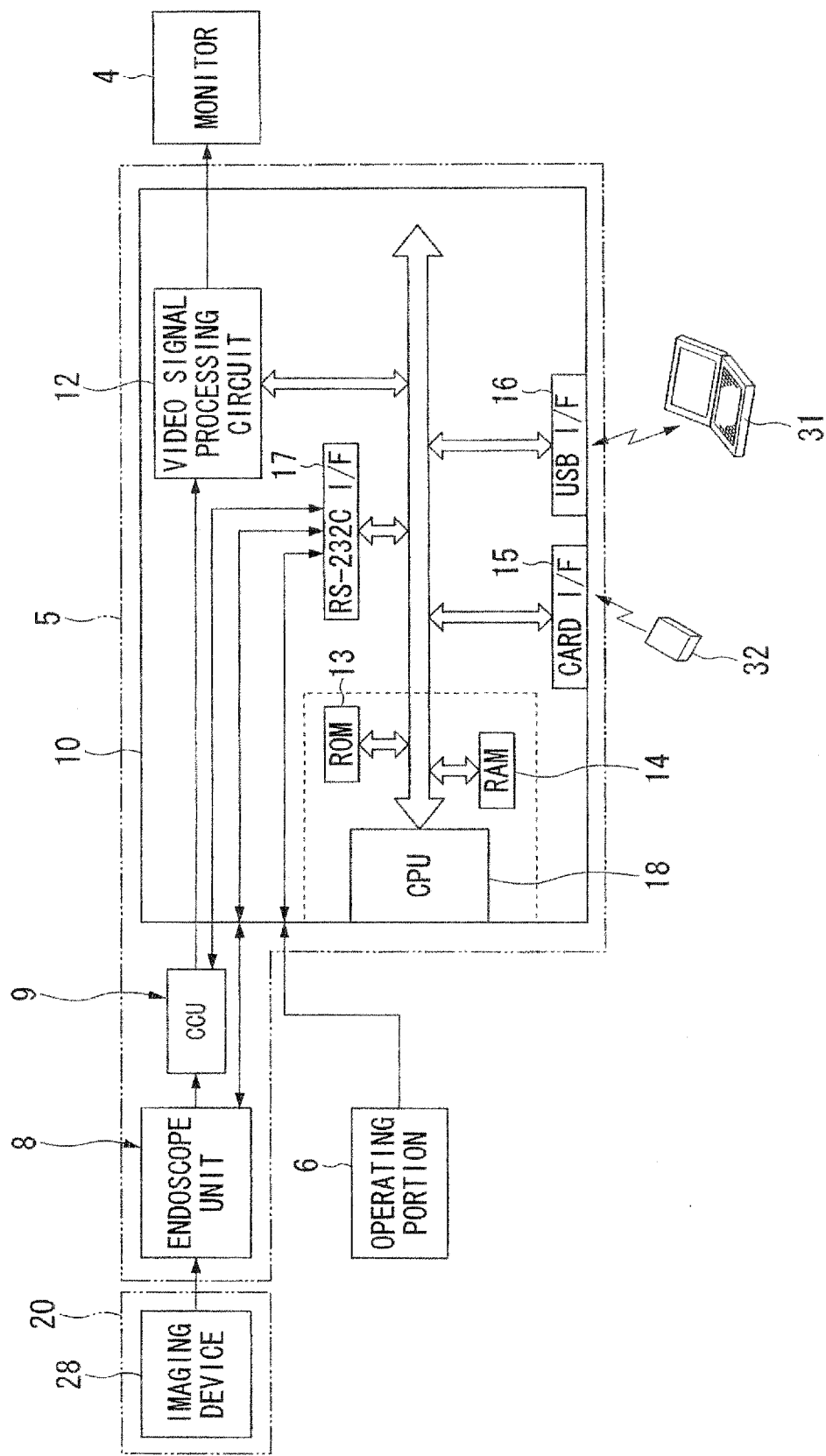
FIG. 2 is a block diagram illustrating the internal configuration of the endoscope apparatus according to the embodiment of the invention.

As shown in FIG. 2, an endoscope unit 8, a CCU 9 (camera control unit), and a control unit 10 are provided in the housing 5. A proximal end of the inserted portion 20 is connected to the endoscope unit 8. The endoscope unit 8 is configured to include a light source driving device, which drives a light source (LED 29) built in the tip portion 21, and a bending device for bending the bent portion 22 provided in the inserted portion 20.

A imaging device 28 and the LED 29 are built in the tip portion 21. The imaging device 28 generates an image signal by performing photoelectric conversion of a subject image formed through the optical adapter. The image signal output from the imaging device 28 is input to the CCU 9. The image signal is converted into a video signal (image data), such as an NTSC signal, in the CCU 9 and is then supplied to the control unit 10. The LED 29 generates illumination light irradiated to the subject. In the present embodiment, the LED 29 is provided in the tip portion 21. However, the LED 29 may be disposed in the housing 5 so that the illumination light generated by the LED 29 is guided to the tip portion 21 through the optical fiber. In addition, other illumination excluding the LED may be used.

A video signal processing circuit 12 to which a video signal is input, a ROM 13, a RAM 14, a card I/F 15 (card interface), a USB I/F 16 (USB interface), an RS-232C I/F 17 (RS-232C interface), and a CPU 18 that executes these various functions on the basis of a main program and performs various controls are provided in the control unit 10.

The CCU 9 and the endoscope unit 8 are connected to the RS-232C I/F 17. In addition, the operating portion 6 which performs control and operation instructions of the CCU 9, endoscope unit 8, and the like is connected to the RS-232C I/F 17. When a user operates the operating portion 6, a communication required in controlling the CCU 9 and the endoscope unit 8 is performed on the basis of the operation.

The USB I/F 16 is an interface for electrically connecting the control unit 10 and a personal computer 31 with each other. By connecting the control unit 10 with the personal computer 31 trough the USB I/F 16, various kinds of instruction controls, such as an instruction to display an endoscope image at the side of the personal computer 31 or image processing at the time of measurement can be performed. In addition, input and output of various kinds of control information or data, which is required for processing, between the control unit 10 and the personal computer 31 can be performed.

In addition, a memory card 32 can be freely attached to the card I/F 15 or detached from the card I/F 15. By mounting the memory card 32 in the card I/F 15, capturing of data such as control processing information or image information stored in the memory card 32 into the control unit 10 or recording of data such as control processing information or image information into the memory card 32 can be performed according to the control of the CPU 18.

In order to display a mixed image obtained by mixing an endoscope image based on the video signal supplied from the CCU 9 with an operation menu using a graphic, the video signal processing circuit 12 performs processing for mixing a graphic image signal based on the operation menu, which is generated by the control of the CPU 18, with the video signal from the CCU 9, processing required for display the mixed image on the screen of the monitor 4, and the like and supplies the display signal to the monitor 4. In addition, the video signal processing circuit 12 may also perform processing for simply displaying an endoscope image or an image of an operation menu, independently. Accordingly, the endoscope image, the operation menu image, or the mixed image obtained by mixing the endoscope image with the operation menu image is displayed on the screen of the monitor 4.

The CPU 18 controls an operation of the entire endoscope apparatus 1 by executing a program stored in the ROM 13 in order to control various circuit portions to perform desired processings. The CPU 18 uses the RAM 14 as a working area for temporarily storing data.

Figure 3:
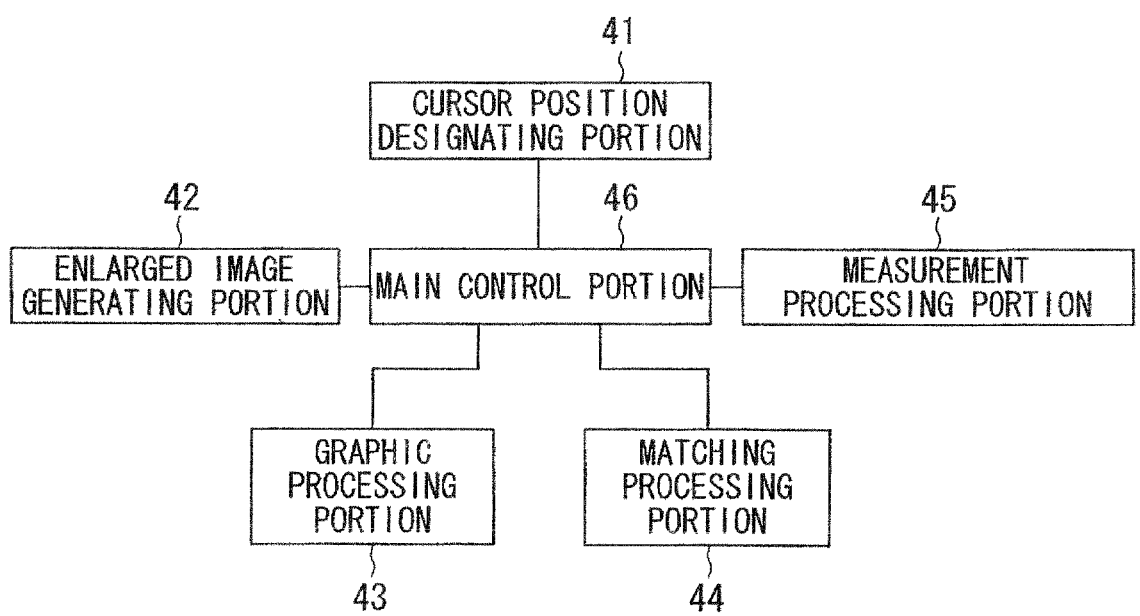
FIG. 3 is a block diagram illustrating the functional configuration of a CPU provided in the endoscope apparatus according to the embodiment of the invention.

FIG. 3 shows the functional configuration of the CPU 18. A cursor position designating portion 41 (designating portion) designates a position (cursor position) at which a cursor is displayed in the image displayed on the monitor 4, on the basis of the result when the user has operated a cursor moving switch of the operating portion 6. An enlarged image generating portion 42 (image processing portion) generates data of an enlarged image obtained by enlarging an image in a predetermined region including the cursor position designated by the cursor position designating portion 41. A graphic processing portion 43 generates a graphic image signal for displaying on the display screen various kinds of information displayed by characters, numeric values, etc., the icon of a cursor, and the like.

A matching processing portion 44 performs matching processing for calculating a position of a corresponding point on a right image corresponding to the cursor position on a left age designated by the cursor position designating portion 41. A measurement processing portion 45 executes processing for calculating the three-dimensional coordinates on the basis of the principle of triangulation or measurement processing for calculating the length, area, and the like of the subject. A main control portion 46 controls assignment of processing to each of the cursor position designating portion 41, the enlarged image generating portion 42, the graphic processing portion 43, the matching processing portion 44, and the measurement processing portion 45, and controls the overall operation of the endoscope apparatus 1.

Figure 23:
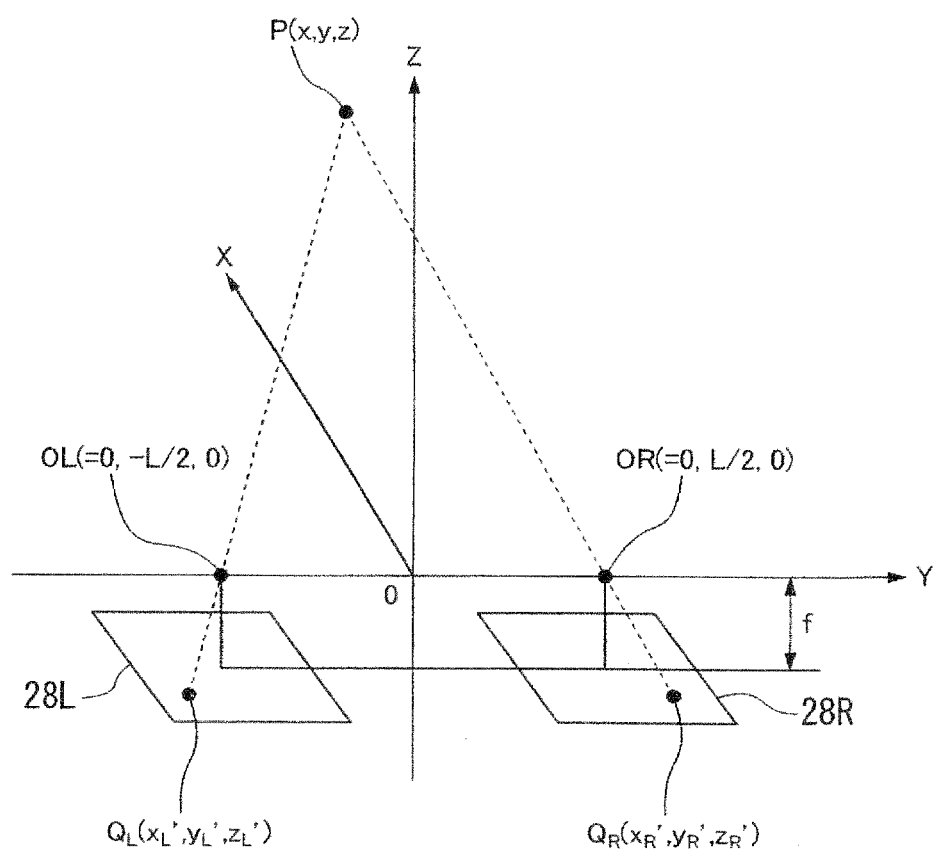
FIG. 23 is a reference view for explaining the method of calculating the three-dimensional coordinates of a measurement point using stereo measurement.
Figure 24:
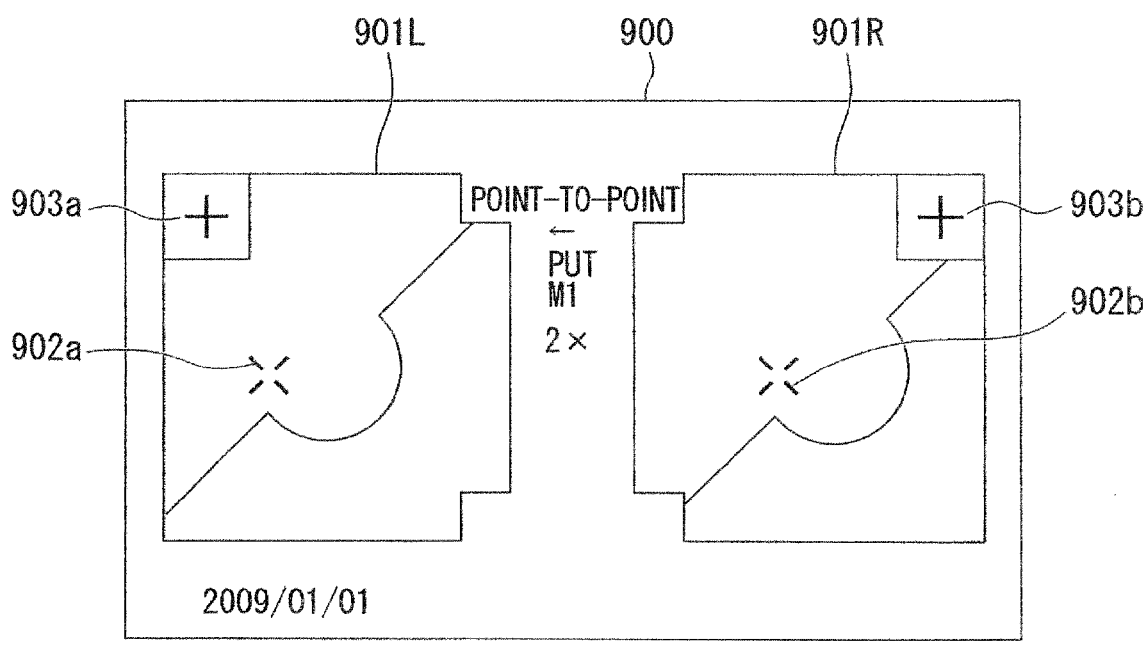
FIG. 24 is a view illustrating a display screen of a known endoscope apparatus.

Next, the basic principle of the measurement in the present embodiment will be described. FIG. 23 shows the positional relationship between two left and right images on the three-dimensional spatial coordinate system with x, y, and z axes. FIG. 23 shows a state where a point P, which is an object for measuring a distance (object distance) to the subject, is imaged on a right imaging surface 28R and a left imaging surface 28L of the imaging device 28. In FIG. 23, it is assumed that points OR and OL are main points of the optical system, a distance f is a focal length, points QR and QL are image locations of the point P, and a distance L is the distance between the point OR and the point OL. In FIG. 23, expression (1) is obtained from the straight line QR-OR.

$$x/xR=\{y-(L/2)\}/\{yR-(L/2)\}=z/(-f) \quad (1)$$

In addition, expression (2) is obtained from the straight line QL-OL.

$$x/xL=\{y+(L/2)\}/\{yL+(L/2)\}=z/(-f) \quad (2)$$

The three-dimensional coordinates of the point P are obtained by solving the expression for x, y and z. As a result, the distance (object distance) from the point OR or the point OL to the subject is calculated. In addition, the three-dimensional length or the three-dimensional area can be calculated by calculating the three-dimensional coordinates of the point P for a plurality of measurement points and performing various operations using the three-dimensional coordinates.

Figure 9:
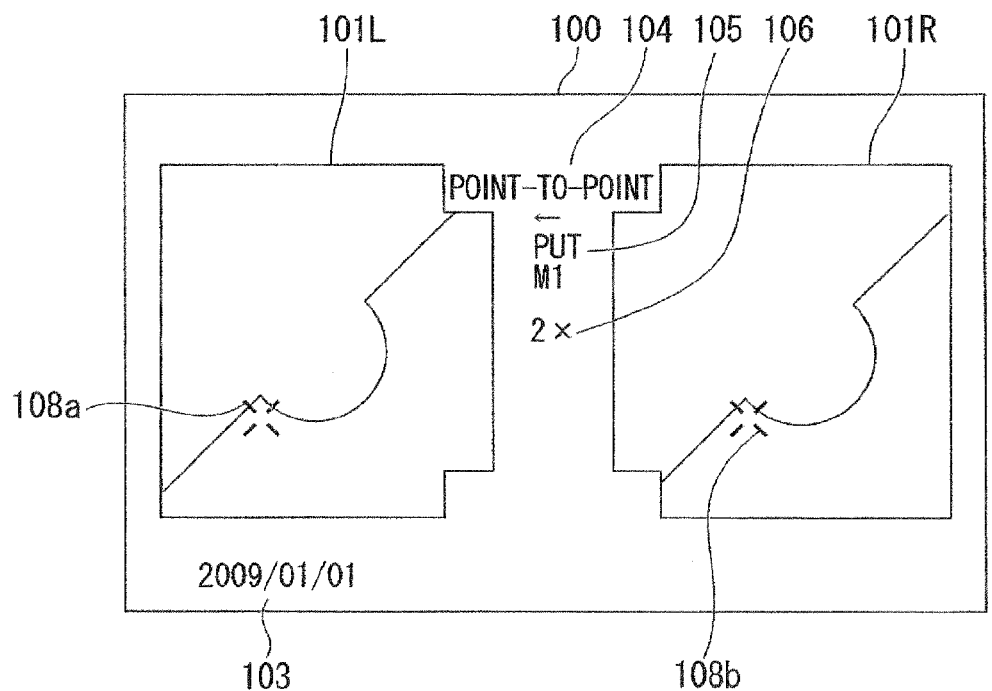
FIG. 9 is a view illustrating a display screen of the endoscope apparatus according to the embodiment of the invention.

Next, the display screen (display portion) of the present embodiment will be described. FIG. 9 shows a display screen 100 at the start of a measurement mode. A pair of left and right images 101L and 101R with parallax, date and time information 103, measurement operation information 104, message information 105, magnifying power information 106, cursors 108a and 108b, and the like are displayed on the display screen 100.

The display screen 100 is configured to include a display region, which is provided in an I-shape in upper, lower, and middle parts of the screen of the display portion 4, and two approximately rectangular display regions excluding the I-shaped display region. A left image 101L is displayed in the left display region shown in the drawing, and a right image 101R is similarly displayed in the right display region. The date and time information 103 is displayed in the lower part of the I-shaped display region. The measurement operation information 104, the message information 105, the magnifying power information 106, object distance information 107 (FIG. 12), and the like are displayed in the middle part of the I-shaped display region. The cursor 108a is displayed on the left image 101L so as to overlap the left image 101L, and the cursor 108b is displayed on the right image 101R so as to overlap the right image 101R.

The measurement operation information 104 displays the type of measurement operation, such as the distance between two points, the depth, the area, or the angle. The present embodiment describes the measurement operation of the distance between two points being performed.

The message information 105 displays information on the operation or measurement as various kinds of text information or numerical information. For example, in FIG. 9, operation guidance (example: "PUT M1" means input of a measurement point of a first point) is displayed.

The magnifying power information 106 displays the magnifying power of image displayed in a zoom window which will be described later.

The cursors 108a and 108b are used to input a measurement point on the display screen 100 The position of the cursor 108a is calculated by the cursor position designating portion 41 according to the operation input from the cursor moving switch of the operating portion 6. The position of the cursor 108b is calculated by the matching processing portion 44 on the basis of the position of the cursor 108a.

Figure 10:
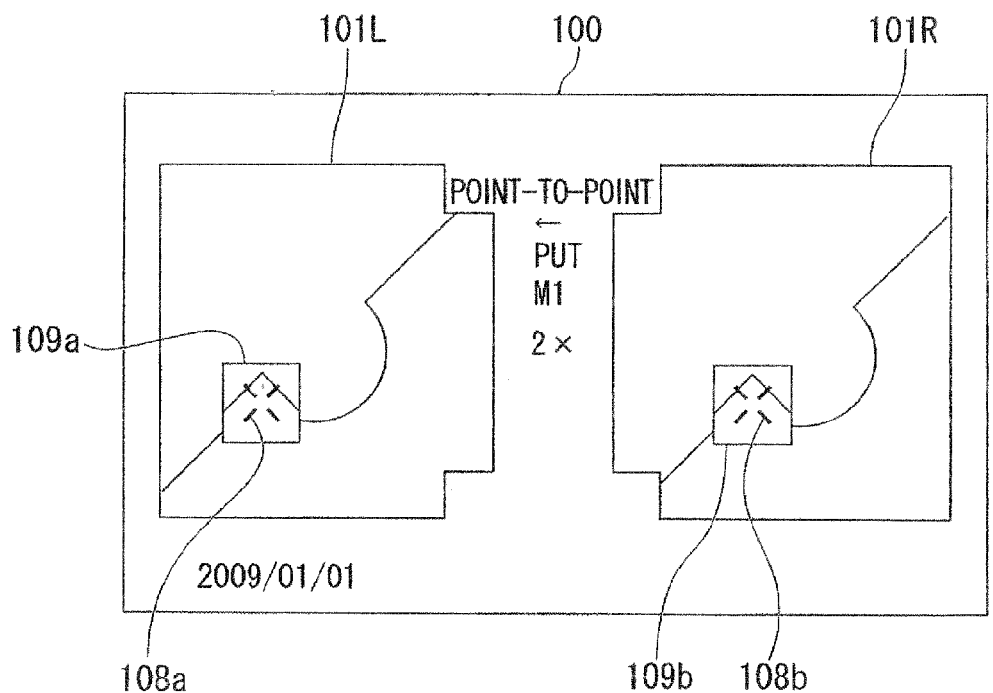
FIG. 10 is a view illustrating a display screen of the endoscope apparatus according to the embodiment of the invention.

When the zoom switch of the operating portion 6 is operated and display of the zoom window is instructed, zoom windows 109a and 109b are displayed as shown in FIG. 10 The zoom window 109a is displayed in the left image 101L, and the zoom window 109b is displayed in the right image 101R.

The cursor 108a and an enlarged image, which is obtained by enlarging an image within a predetermined range around the cursor 108a in the left image 101L, are displayed in the zoom window 109a. The cursor 108b and an enlarged image, which is obtained by enlarging an image within a predetermined range around the cursor 108b in the right image 101R, are displayed in the zoom window 109b. The size of each of the zoom windows 109a and 109b is 60×60 pixels, for example. When the magnifying power is 2×, enlarged images obtained by enlarging, for example, images within the range of 30×30 pixels on the left and right images 101L and 101R are displayed in the zoom windows 109a and 109b, respectively. The shapes of the cursors 108a and 108b displayed together with the zoom windows 109a and 109b may be different from those of the cursors 108a and 108b when the zoom windows 109a and 109b are not displayed.

The user can change the magnifying power of the enlarged image displayed in each of the zoom windows 109a and 109b by operating the zoom switch of the operating portion 6. The zoom switch is configured to include a teleswitch for enlargement and a wide switch for reduction. The magnifying power is increased when the teleswitch is operated in a state where the zoom windows 109a and 109b are displayed. In addition the magnifying power is decreased when the wide switch is operated in a state where the zoom windows 109a and 109b are displayed. When the magnifying power is 1×, the zoom windows 109a and 109b are not displayed.

Figure 11:
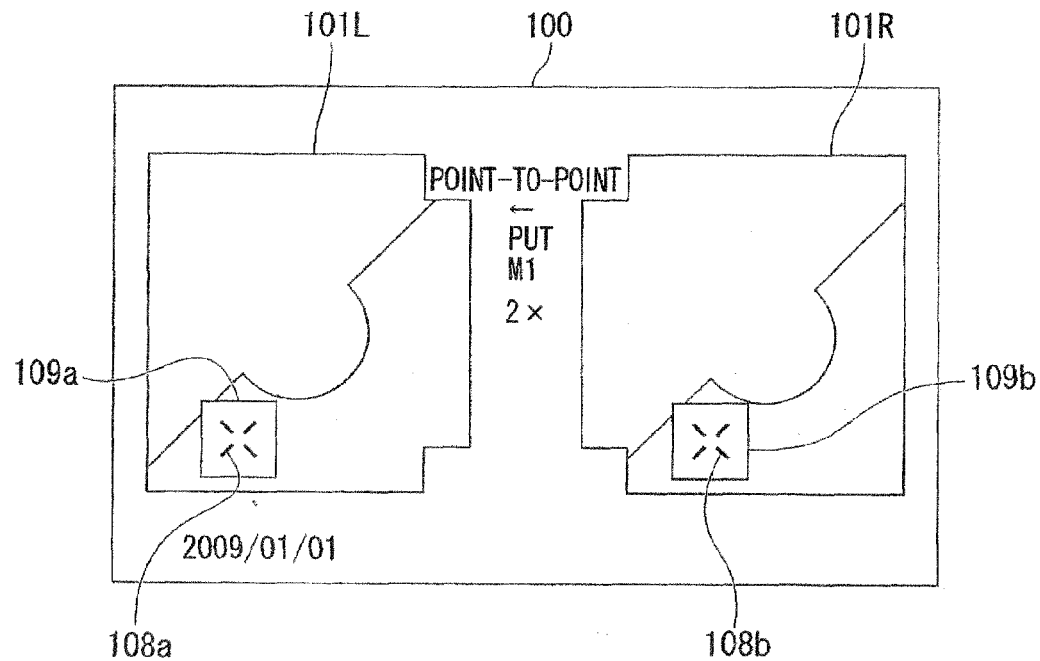
FIG. 11 is a view illustrating a display screen of the endoscope apparatus according to the embodiment of the invention.

In addition, the user can move the zoom windows 109a and 109b together with the cursors 108a and 108b by operating the cursor moving switch of the operating portion 6. For example, when an instruction to move the cursor 108*a* downward is input from the state of FIG. 10 the zoom windows 109*a* and 109*b* move downward together with the cursors 108*a* and 108*b*, as show in FIG. 11. In order to reduce the processing load of the endoscope apparatus 1, the zoom windows 109*a* and 109*b* are not displayed during the movement of the cursor 108*a*. The zoom windows 109*a* and 109*b* are displayed when the cursor 108*a* stops.

Hereinafter, the transition of the display screen will be described using the point-to-point measurement as an example. In the point-to-point measurement, a first measurement point and a second measurement point are set and the distance between the two points is calculated on the basis of the two measurement points.

Figure 12:
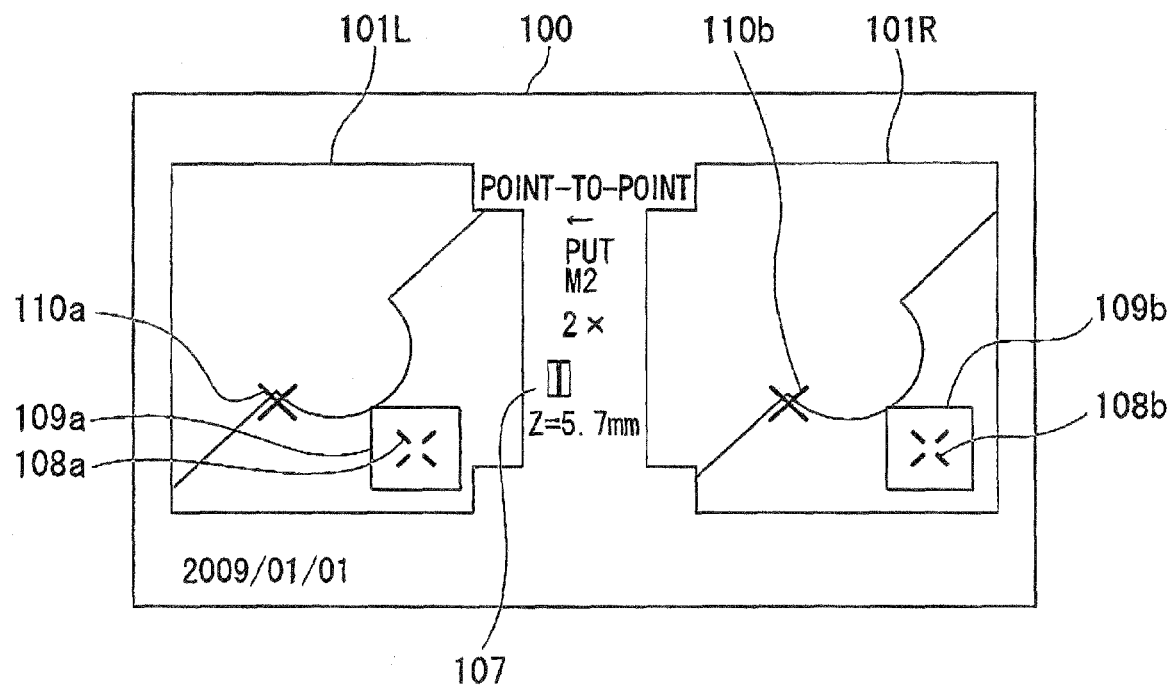
FIG. 12 is a view illustrating a display screen of the endoscope apparatus according to the embodiment of the invention.

When the user performs an operation of deciding a measurement point with the cursor moving switch of the operating portion 6 in a state where the cursor 108*a* is displayed at the desired position at which the user wants to set a first measurement point, the first measurement point is set at a position within a region of the zoom window 109*a*, for example, at the position where the cursor 108*a* is displayed. Second overlay information, such as the first measurement point, is set on the basis of first overlay information, such as the zoom window 109*a* or the cursor 108*a*. Moreover, on the display screen, the first overlay information may move with respect to the second overlay information. FIG. 12 shows a state where the cursor 108*a* and the zoom window 109*a* have moved with respect to the first measurement point after the first measurement point was set on the basis of the zoom window 109*a*. A first measurement point 110*a* is displayed on the left image 101L, and a corresponding point 110*b* corresponding to the measurement point 110*a* is displayed on the right image 101R. When the measurement point 110*a* is set, the zoom windows 109*a* and 109*b* become not to be displayed. If necessary, the user may display the zoom windows 109*a* and 109*b* again as shown in FIG. 12 by operating the zoom switch of the operating portion 6.

In addition, when the measurement point 110*a* is set, the object distance is calculated and the object distance information 107 is displayed. The object distance information 107 indicates the degree of the distance between the tip portion 21 of the inserted portion 20 and the subject. This object distance is calculated by the measurement processing portion 45. The object distance is expressed by nine square indicators, and a smaller number of square indicators are displayed as the object distance becomes smaller.

Image matching information may be displayed instead of the object distance information. The image matching information indicates the matching degree between a designated position of one image (in this example, the left image 101L) input by the examiner and the corresponding position of the other image (in this example, the right image 101R). This matching degree is calculated by the matching processing portion 44. The matching degree is expressed by nine square indicators, and a smaller number of square indicators are displayed as the matching degree becomes stronger (as images at the designated position further match each other).

In addition, although object distance information 107 is expressed by the square indicators in this example, it may be expressed by numeric values or in other forms.

Then, when the user performs an operation of deciding a measurement point with the cursor moving switch of the operating portion 6 in a state where the cursor 108*a* is displayed at the desired position at which the user wants to set a second measurement point, the second measurement point is set at the position where the cursor 108*a* is displayed. When the second measurement point is set, the distance between the two points is calculated and displayed on the display screen 100 as a measurement result.

Figure 13:
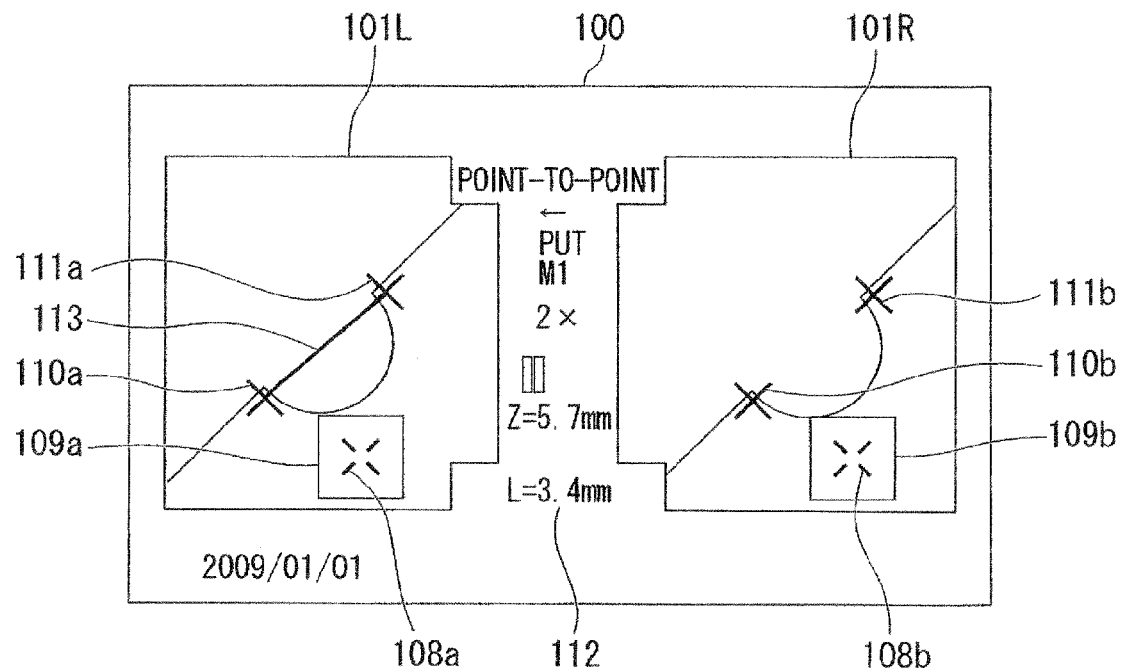
FIG. 13 is a view illustrating a display screen of the endoscope apparatus according to the embodiment of the invention.

FIG. 13 shows a state where the second measurement point is set. A second measurement point 111*a* is displayed on the left image 101L, and a corresponding point 111*b* corresponding to the measurement point 111*a* is displayed on the right image 101R. In addition, measurement result informational 112 indicating the result of the point-to-point measurement is displayed in the middle part of the I-shaped display region. In addition, a measurement line 113 which connects the measurement point 110*a* and the measurement point 111*a* is displayed on the left image 101L.

When the measurement point 111*a* is set, the zoom windows 109*a* and 109*b* become not to be displayed. If necessary, the user may display the zoom windows 109*a* and 109*b* again as shown in FIG. 13 by operating the zoom switch of the operating portion 6. Moreover, in the point-to-point measurement of the present embodiment, the point-to-point measurement may be performed again by setting the first and second measurement points again in a state where the measurement points 110*a* and 111*a* and the corresponding points 110*b* and 111*b* are displayed after the distance between two points is calculated and the measurement result information 112 is displayed. Accordingly, the cursors 108*a* and 108*b* and the zoom windows 109*a* and 109*b* can move with respect to the measurement points 110*a* and 111*a*, the corresponding points 110*b* and 111*b*, and the measurement result information 112.

Figure 4:
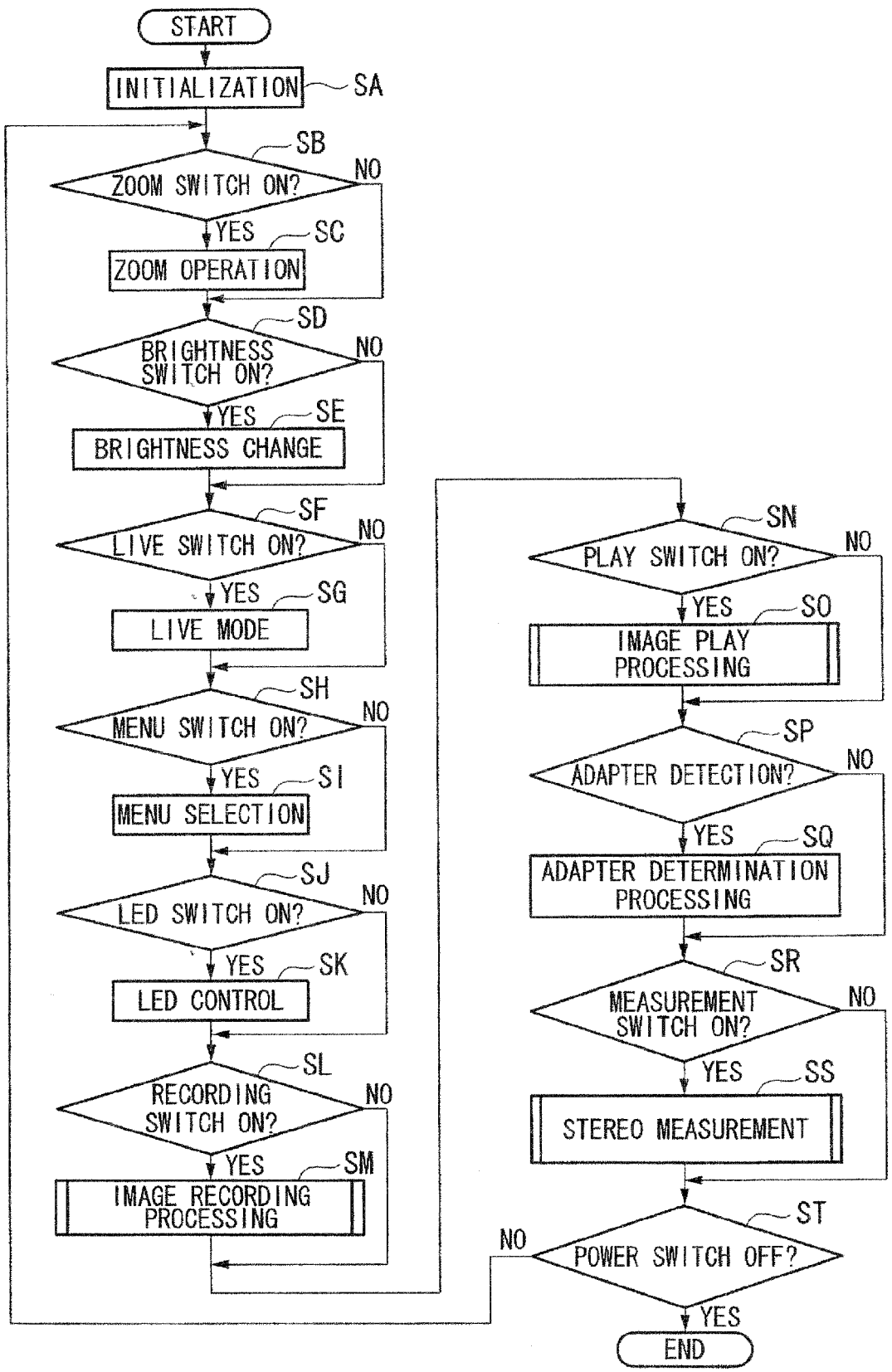
FIG. 4 is a flow chart illustrating the procedure of an operation of the endoscope apparatus according to the embodiment of the invention.

Next, an operation of the endoscope apparatus 1 will be described with reference to the flow chart. FIG. 4 shows the overall operation of the endoscope apparatus 1. When the endoscope apparatus 1 is started, the main control portion 46 executes initialization (step SA). Then, the main control portion 46 monitors a signal input from the operating portion 6 through the RS-232C I/F 17 and determines whether or not the zoom switch for image magnification change is ON (step SB). When the zoom switch is ON, the main control portion 46 instructs the magnification change in electronic zoom processing for enlarging the image to the video signal processing circuit 12 (step SC). Then, the process proceeds to step SD. In addition, when the zoom switch is OFF in step SB, the process proceeds to step SD.

Then, the main control portion 46 monitors a signal input from the operating portion 6 through the RS-232C I/F 17 and determines whether or not a brightness switch for image brightness change is ON (step SD). When the brightness switch is ON, the main control portion 46 instructs the brightness change of the whole image to the video signal processing circuit 12 (step SE). Then, the process proceeds to step SF. In addition, when the brightness switch is OFF in step SD, the process proceeds to step SF.

Then, the main control portion 46 monitors a signal input from the operating portion 6 through the RS-232C I/F 17 and determines whether or not a live switch for changing the measurement mode to the live mode is ON (step SF). The endoscope apparatus 1 can operate in a plurality of operation modes (a live mode, a recording mode, a measurement mode, and a play mode). The live mode is a mode in which a moving image imaged by the endoscope 2 is displayed in real time. The recording mode is a mode in which image data imaged by the endoscope 2 is recorded in the memory card 32. The measurement mode is a mode in which point-to-point measurement or the like is executed on the basis of the image data imaged by the endoscope 2. The play mode is a mode in which image data recorded in the memory card 32 is read and an image of the image data is displayed. When the live switch is ON in a state where one of the recording mode, the measurement mode, and the play mode is operating, the main control portion 46 changes the operation mode to the live mode and instructs an operation in the live mode to each portion of the endoscope apparatus 1. Then, the imaging device 28 images a subject and generates an image signal. The CCU 9 converts the image signal into a video signal. The video signal processing circuit 12 generates a display signal by mixing the video signal with the graphic image signal from the graphic processing portion 43 and outputs it to the monitor 4. The monitor 4 displays the image on the basis of the display signal (step SG). Then, the process proceeds to step SH. In addition, when the live switch is OFF in step SF, the process proceeds to step SH.

Then, the main control portion 46 monitors a signal input from the operating portion 6 through the RS-232C I/F 17 and determines whether or not a menu switch is ON (step SH). When the menu switch is ON, the graphic processing portion 43 generates a graphic image signal for operation menu display and outputs it to the video signal processing circuit 12 (step SI). Then, the process proceeds to step SJ. In addition, when the menu switch is OFF in step SH, the process proceeds to step SJ.

Then, the main control portion 46 monitors a signal input from the operating portion 6 through the RS-232C I/F 17 and determines whether or not an LED switch for turning on the LED in the optical adapter is ON (step SJ). When the LED switch is ON, the main control portion 46 instructs starting of a lighting device to the endoscope unit 8 (step SK). Then, the process proceeds to step SL. In addition, when the LED switch is OFF in step SJ, the process proceeds to step SL.

Then, the main control portion 46 monitors a signal input from the operating portion 6 through the RS-232C I/F 17 and determines whether or not a recording switch for image recording is ON (step SL). When the recording switch is ON, the main control portion 46 changes the operation mode to the recording mode and records image data acquired from the video signal processing circuit 12 in the memory card 32 trough the card I/F 15 (step SM). Details of step SM will be described later. Then, the process proceeds to step SN. In addition, when the recording switch is OFF in step SL, the process proceeds to step SN.

Then, the main control portion 46 monitors a signal input from the operating portion 6 through the RS-232C I/F 17 and determines whether or not a play switch for image play is ON (step SN). When the play switch is ON, the main control portion 46 changes the operation mode to the play mode, reads image data from the memory card 32 through card I/F 15, and outputs it to the video signal processing circuit 12 (step SO). Details of step SO will be described later. Then, the process proceeds to step SP. In addition, when the play switch is OFF in step SN, the process proceeds to step SP.

Then, the ma n control portion 46 monitors a signal input through a signal line (not shown) connected to the tip portion 21 of the inserted portion 20 and determines whether or not an optical adapter is attached (step SP). When the optical adapter is attached, the main control portion 46 checks the type of the optical adapter, reads environmental data corresponding to the type from the memory card 32 through the card I/F 15, and stores it in the RAM 14 (step SQ). Checking the type of the optical adapter is performed by detecting the resistance value, which changes according to the type of the optical adapter, provided in the optical adapter, for example. Then, the process proceeds to step SR. In addition, when the optical adapter is not provided in step SP, the process proceeds to step SR.

Then, the main control portion 46 monitors a signal input from the operating portion 6 through the RS-232C I/F 17 and determines whether or not a measurement switch for stereo measurement is ON (step SR). When the measurement switch is ON, the main control portion 46 changes the operation mode to the measurement mode and makes each functional portion of the CPU 18 execute stereo measurement (step SS). Details of step SS will be described later. Then, the process proceeds to step ST. In addition, when the measurement switch is OFF in step SR, the process proceeds to step ST.

Then, the main control portion 46 monitors a signal input from the operating portion 6 through the RS-232C I/F 17 and determines whether or not a power switch for a power source is ON (step ST). When the power switch is OFF, the endoscope apparatus 1 ends the operation. In addition, when the power switch is ON in step ST, the process returns to step SB.

Figure 5:
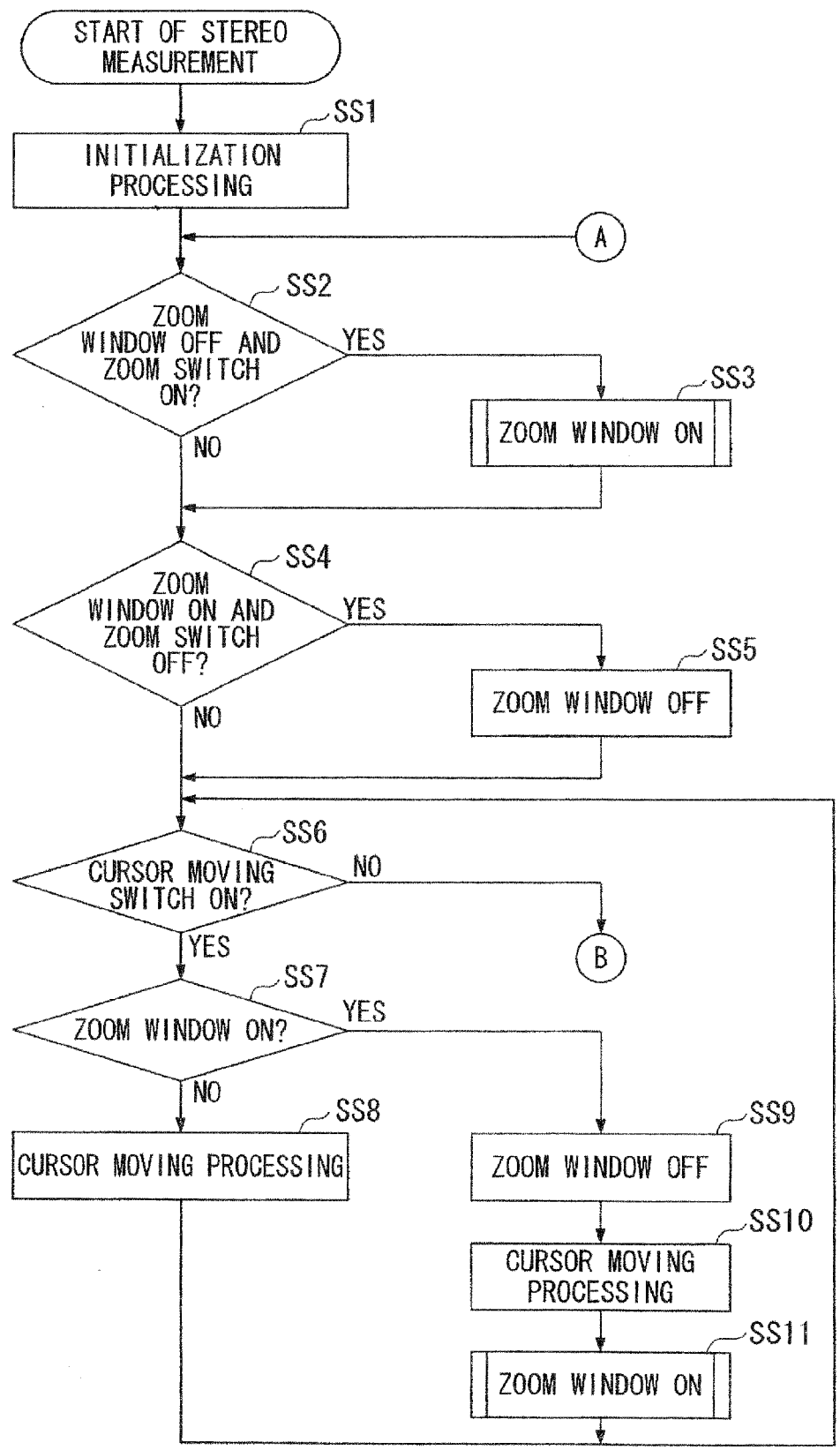
FIG. 5 is a flow chart illustrating the procedure of an operation of the endoscope apparatus according to the embodiment of the invention.
Figure 6:
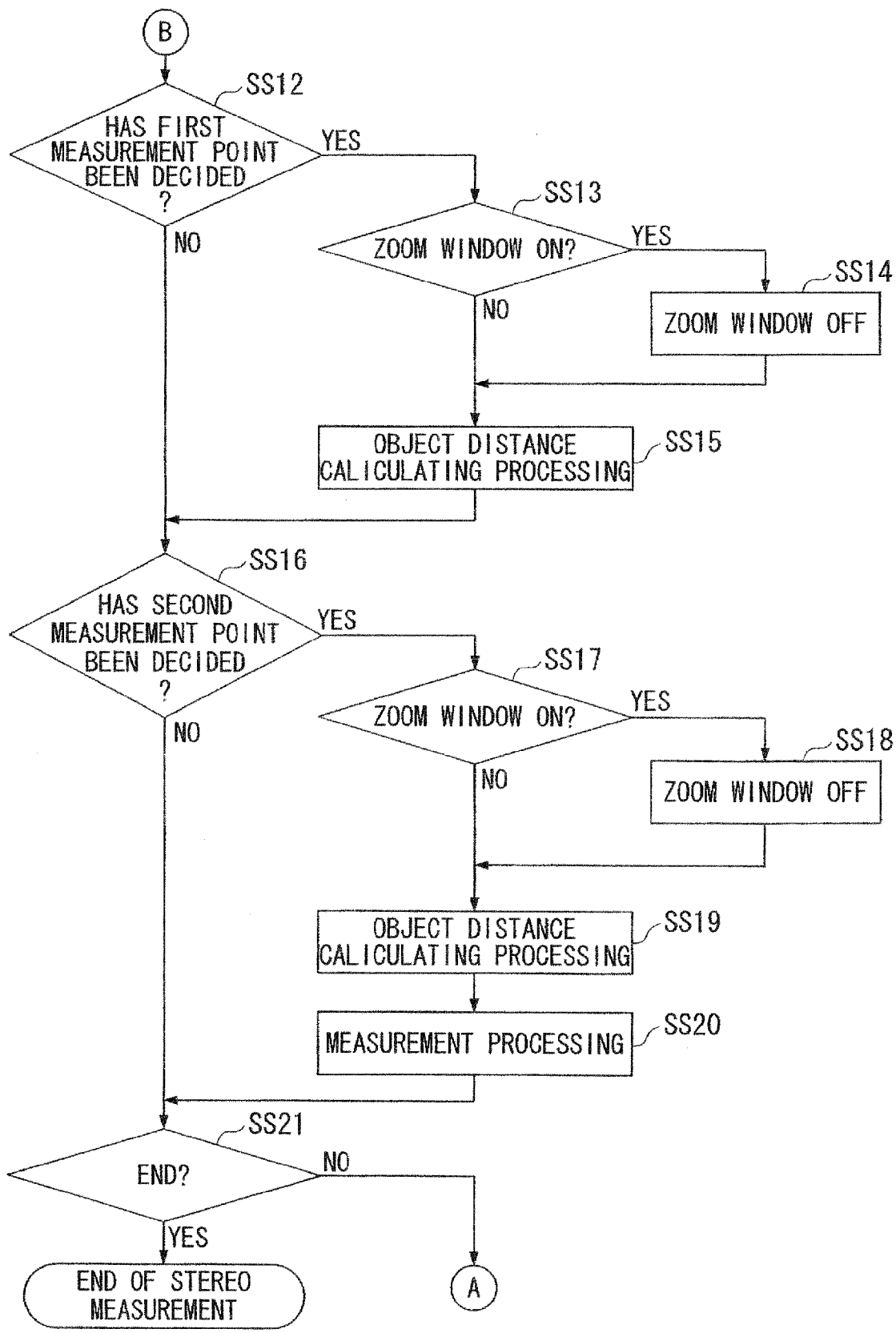
FIG. 6 is a flow chart illustrating the procedure of an operation of the endoscope apparatus according to the embodiment of the invention.
Figure 7:
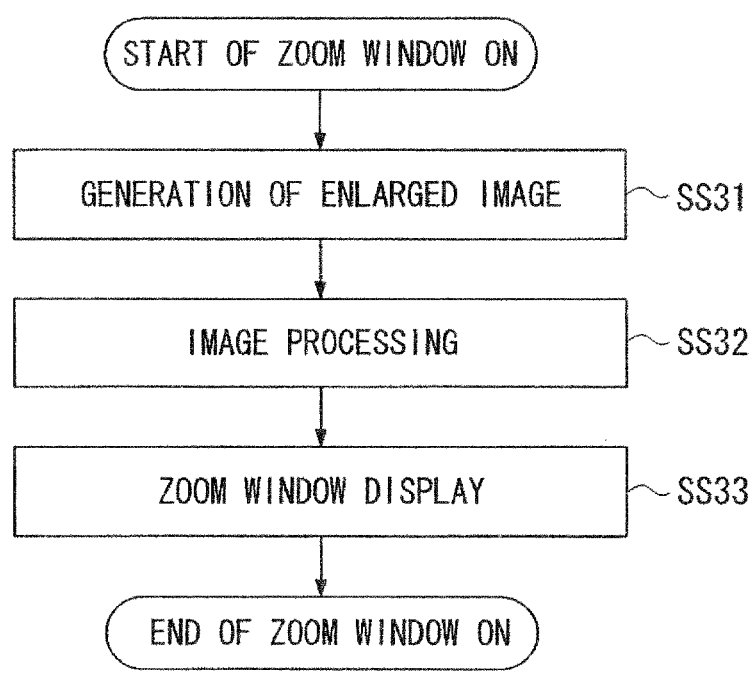
FIG. 7 is a flow chart illustrating the procedure of an operation of the endoscope apparatus according to the embodiment of the invention.

Next, the details of the above-described step SS (stereo measurement) will be described. The point-to-point measurement is exemplified below. FIGS. 5 to 7 show the procedure of stereo measurement. First, initialization processing is executed (step SS1). In the initialization processing, various variables stored in the RAM 14 are initialized. The various variables stored in the RAM 14 include a variable indicating a display/non-display state of a zoom window, a variable indicating the current cursor position, a variable indicating a state of decision/non-decision of a measurement point, a variable indicating the position of the decided measurement point, and the like. Moreover, the initialization processing is performed such that the display screen for measurement is displayed on the monitor 4 but the zoom window is not displayed (for example, FIG. 9).

Then, the main control portion 46 determines whether or not the zoom window is displayed referring to the zoom window state variable stored in the RAM 14. Then, the main control portion 46 monitors a signal input from the operating portion 6 through the RS-232C I/F 17 and determines whether or not the zoom switch is ON (step SS2).

When the zoom window is not displayed and the zoom switch is ON, processing for displaying the zoom window is executed (step SS3). Details of step SS3 will be described later. By execution of the processing of step SS3, the zoom window is displayed on the display screen (for example, FIG. 10). By the processing of step SS3, the zoom window state variable in the RAM 14 is updated to the value indicating 'display'. The process proceeds to step SS4 after step SS3. In addition, when the zoom switch is displayed in step SS2 or when the zoom switch is OFF in step SS2, the process proceeds to step SS4.

In step SS4, the main control portion 46 determines whether or not the zoom window is displayed and whether or not the zoom switch is ON similar to step SS2 (step SS4). When the zoom window is displayed and the zoom switch is OFF, processing for making the zoom window not displayed is executed (step SS5). By the processing of step SS5, the zoom window state variable in the RAM 14 is updated to the value indicating 'non-display'. The process proceeds to step SS6 after step SS5. In addition, when the zoom switch is not displayed in step SS4 or when the zoom switch is ON in step SS4, the process proceeds to step SS6.

FIG. 5 shows that the processing of steps SS2 to SS5 is executed between steps SS1 and SS6. However, when interruption occurs by the operation of the zoom switch of the operating portion 6, the processing of steps SS2 to SS5 is executed at any processing timing of FIGS. 5 to 7. After the processing of steps SS2 to SS5 ends, processing is resumed from the state immediately before the processing of steps SS2 to SS5 is executed.

In step SS6, the main control portion 46 monitors a signal input from the operating portion 6 through the RS-232C I/F 17 and determines whether or not the cursor moving switch is ON (step SS6). When the cursor moving switch is OFF, the process proceeds to step SS12. In addition, when the cursor moving switch is ON, the main control portion 46 determines whether or not the zoom window is displayed referring to the zoom window state variable stored in the RAM 14 (step SS7).

When the zoom window is not displayed, processing for moving the cursor on the display screen is executed (stop SS8). Details of the processing of step SS8 will be described below. The cursor position designating portion 41 calculates the next cursor position by adding the movement amount, which is designated by the operation of the cursor moving switch, to the current cursor position referring to the current cursor position stored in the RAM 14. The calculated next cursor position is stored in the RAM 14 as the current cursor position.

The matching processing portion 44 calculates the position of a corresponding point on the right image corresponding to the 'next cursor position' on the left image by matching processing using image pattern matching. The graphic processing portion 43 generates a graphic image signal for displaying the icon of a cursor and the like. The video signal processing circuit 12 generates a display signal by mixing the graphic image signal with the video signal from the CCU 9 such that the cursors are displayed at the position on the left image designated by the cursor position designating portion 41 and the position on the right image calculated by the matching processing portion 44, and outputs it to the monitor 4. The monitor 4 displays an image on the basis of the display signal.

As a result the cursor is displayed together with the image of the subject imaged by the endoscope 2. While movement of the cursor is being instructed by the cursor moving switch, the above processing is repeatedly executed and the cursor moves on the display screen. When the input of the instruction to move the cursor is stopped, the process proceeds to step SS12.

When the zoom window is displayed in step SS7, processing for making the zoom window not displayed is executed (step SS9). Then, similar to step SS8, processing for moving the cursor on the display screen is executed (step SS10). While movement of the cursor is being instructed by the cursor moving switch, the processing described in step SS10 is repeatedly executed and the cursor moves on the display screen. When the input of the instruction to move the cursor is stopped, the process proceeds to step SS11.

In step SS11, processing for displaying the zoom window is executed similar to step SS3 (step SS11). Details of step SS11 will be described later. By execution of the processing of step SS11, the zoom window is displayed on the display screen. The process proceeds to step SS12 after step SS11.

In step SS12 shown in FIG. 6, the main control portion 46 monitors a signal input from the operating portion 6 through the RS-232C I/F 17 and determines whether or not there has been the input of a decision switch for deciding a first measurement point (step SS12). When the first measurement point is not decided (decision switch is not input), the process proceeds to step SS16. In addition, when the first measurement point has been decided (decision switch has been input), the main control portion 46 determines whether or not the zoom window is displayed referring to the zoom window state variable stored in the RAM 14 (step SS13).

When the zoom window is not displayed, the process proceeds to step SS15. In addition, when the zoom window is displayed, processing for making the zoom window not displayed is executed (step SS14). Then, object distance calculating processing for calculating the object distance is executed (step SS15).

Details of the processing of step SS15 will be described below. The matching processing portion 44 calculates the position of a corresponding point on the right image, which corresponds to the position of the measurement point on the left image stored in the RAM 14, by matching processing using image pattern matching. The measurement processing portion 45 calculates the three-dimensional coordinates (coordinates of the point P of FIG. 23) on the basis of the positions of the measurement point and corresponding point. The measurement processing portion 45 calculates the object distance on the basis of the calculated three-dimensional coordinates. The object distance is a distance from the tip of the endoscope to the subject to be observed (object to be observed). For example, the object distance is calculated as a distance from the imaging device or the objective optical system to the subject to be observed. The calculated object distance is displayed on the display screen (for example, FIG. 12). The process proceeds to step SS16 after step SS15.

In step SS16, the main control portion 46 monitors a signal input from the operating portion 6 through the RS-232C I/F 17 and determines whether or not there has been the input of a decision switch for deciding a second measurement point (step SS16). When the second measurement point is not decided (decision switch is not input), the process proceeds to step SS21. In addition, when the second measurement point has been decided (decision switch has been input), the main control portion 46 determines whether or not the zoom window is displayed referring to the zoom window state variable stored in the RAM 14 (step SS17).

When the zoom window is not displayed, the process proceeds to step SS19. In addition, when the zoom window is displayed, processing for making the zoom window not displayed is executed (step SS18). Then, similar to step SS15, object distance calculating processing for calculating the object distance is executed (step SS19).

Then, measurement processing is executed (step SS20). Details of the processing of step SS20 will be described below. The measurement processing portion 45 calculates the distance between two points on the basis of the three-dimensional coordinates of the first measurement point calculated in step SS15 and the three-dimensional coordinates of the second measurement point calculated in step SS19. The calculated distance between two points is displayed on the display screen (for example, FIG. 13). The process proceeds to step SS21 after step SS20.

In step SS21, the main control portion 46 determines whether or not to end the stereo measurement (step SS21). For example when the instruction to end the stereo measurement has been input, the stereo measurement ends. In addition, when the stereo measurement is not ended, the process returns to step SS2.

Details of the processing of step SS3 and SS11 will be described below (FIG. 7). The enlarged image generating portion 42 extracts data, which corresponds to an image in a predetermined region (for example, a region of 30×30 pixels) on the left image around the cursor position designated by the cursor position designating portion 41, from the image data acquired from the video signal processing circuit 12. In addition, the enlarged image generating portion 42 extracts data, which corresponds to an image in a predetermined region (for example, a region of 30×30 pixels) on the right image around the corresponding point on the right image corresponding to the cursor position on the left image, from the image data acquired from the video signal processing circuit 12. In addition, the enlarged image generating portion 42 executes image enlarging processing on the basis of the extracted data to generate data of the left and right enlarged images (step SS31).

The video signal processing circuit 12 processes the image data so that the left enlarged image generated by the enlarged image generating portion 42 overlaps the predetermined region (for example, a region of 60×60 pixels) on the left image around the cursor position designated by the cursor position designating portion 41. Specifically, the video signal processing circuit 12 executes processing for rewriting data of the image data, which corresponds to the image in the predetermined region (for example a region of 60×60 pixels) on the left image, to the data of the left enlarged image. In addition, the video signal processing circuit 12 processes the image data so that the right enlarged image generated by the enlarged image generating portion 42 overlaps the predetermined region (for example, a region of 60×60 pixels) on the right image around the position of the corresponding point on the right image corresponding to the cursor position designated by the cursor position designating portion 41. Specifically, the video signal processing circuit 12 executes processing for rewriting data of the image data, which corresponds to the image in the predetermined region (for example, a region of 60×60 pixels) on the right image around the corresponding point on the right image, to the data of the right enlarged image (step SS32). As a result, the left and right enlarged images overlap the images of the subject imaged by the endoscope.

Then, the video signal processing circuit 12 generates a display signal by mixing the graphic image signal from the graphic processing portion 43 with the image data processed in step SS32. The graphic image signal includes the icon of a cursor, the frame of a zoom window, and the like. When the measurement point has been decided, the graphic image signal also includes the icon of the decided measurement point and the icon of the corresponding point. In addition, the main control portion 46 controls the video signal processing circuit 12 on the basis of the cursor position designated by the cursor position designating portion 41 and the corresponding point of the cursor position calculated by the matching processing portion 44, such that the video signal processing circuit 12 mixes the image data and the graphic image signal so that the cursors are displayed at the cursor position designated by the cursor position designating portion 41 and the corresponding point. The monitor 4 displays an image on the basis of the display signal generated by the video signal processing circuit 12 (step SS33). As a result, the zoom window and the like are displayed on the display screen.

In the processing shown in FIGS. 5 to 7, when the movement of a cursor is instructed while the zoom window is displayed, the zoom window is not displayed. However, it may be performed as follows. For example, the zoom window may not be displayed when the duration of a state where the cursor moving switch of the operating portion 6 is ON is 0.1 second or more, and the zoom window may move with the cursor while displayed when the duration of the state where the cursor moving switch is ON is less than 0.1 second.

In addition, in the processing shown in FIGS. 5 to 7, the measurement processing is executed after the second measurement point is decided. However, after the first measurement point is decided, the measurement processing may also be executed before the second measurement point is decided. In addition, in the processing shown in FIGS. 5 to 7, the object distance calculating processing is executed after the measurement point is decided. However, the distance measurement processing may be always executed irrespective of whether or not the measurement point has been decided.

In addition, when it is determined that the matching degree between the measurement point on the left image and the corresponding point on the right image is low in steps SS3 and SS11, the zoom window on the right image may not be displayed. Moreover, also when the corresponding point on the right image is located outside the right measurement region as a result of matching using the matching processing portion 44, the zoom window on the right image may not be displayed.

Figure 14:
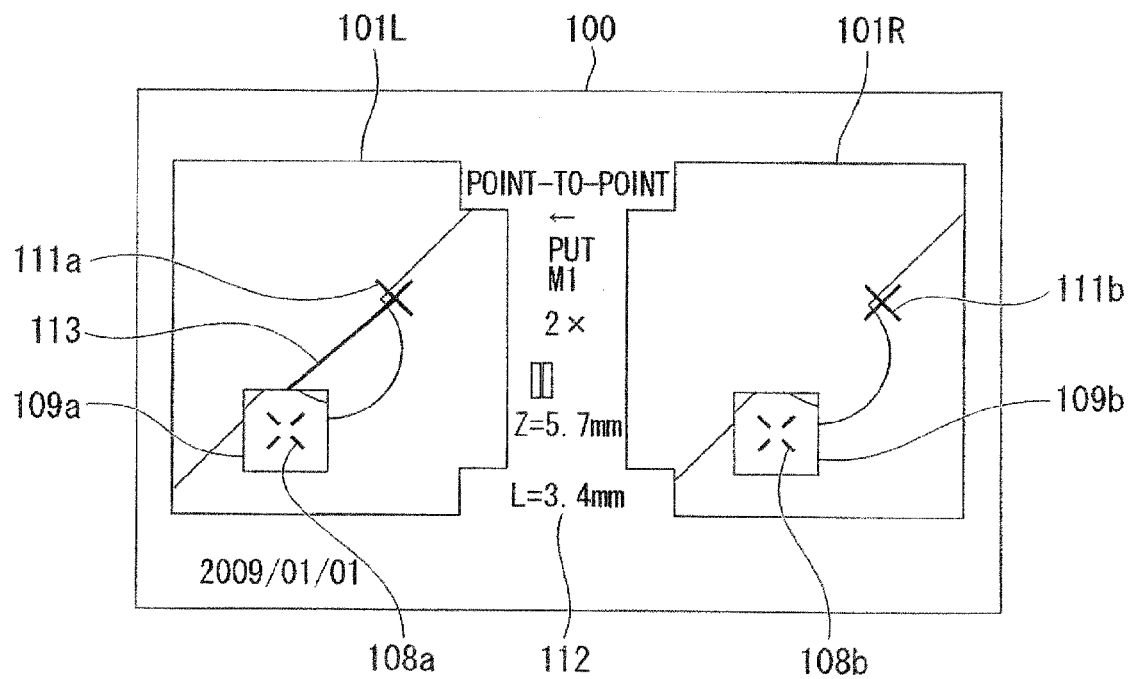
FIG. 14 is a view illustrating a display screen of the endoscope apparatus according to the embodiment of the invention.

Next, a control when the zoom window overlaps other parts in the display screen will be described. Within the left measurement region where the left image is displayed and the right measurement region where the right image is displayed, first overlay information, such as the zoom window 109a or 109b which can move on the left image or right image, is preferentially displayed over second overlay information, such as the measurement points 110a or 11a, the corresponding points 110b and 111b, and the measurement line 113, when the first overlay information overlaps the second overlay information. Here, when the zoom window and the measurement point overlap each other, the zoom window is preferentially displayed over the measurement point. For example, when the zoom windows 109a and 109b have moved near the measurement point 110a and the corresponding point 110b from the state of FIG. 13, the zoom windows 109a and 109b are displayed and the measurement point 110a and the corresponding point 110b are not displayed as shown in FIG. 14. In this case, the graphic processing portion 43 does not generate a graphic image signal of the measurement points and the measurement line within the region where the zoom window is displayed.

The viewability of the zoom window is maintained by displaying the window preferentially over the measurement point as described above.

Figure 15:
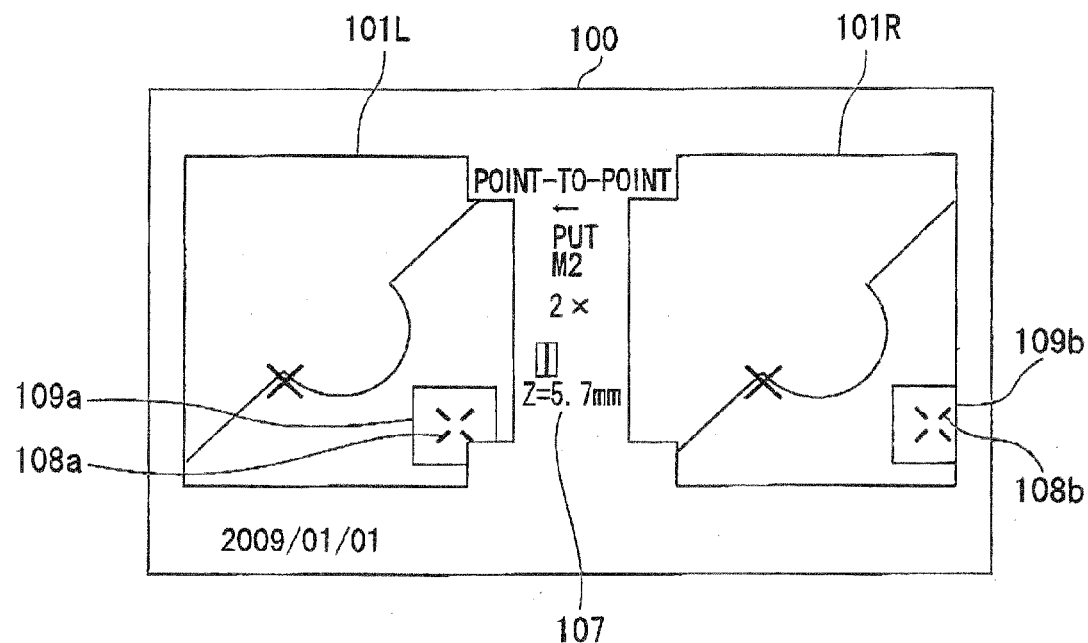
FIG. 15 is a view illustrating a display screen of the endoscope apparatus according to the embodiment of the invention.

In the outside of the left measurement region where the left image is displayed and the right measurement region where the right image is displayed, third overlay information, such as the date and time information 103, the measurement operation information 104, the message information 105, the magnifying power information 106, the object distance information 107, and the measurement result information 112, is displayed preferentially over the first overlay information. Here, the other information is displayed preferentially over the zoom window. For example, when the zoom window 109a has moved to the right end of the left measurement region and the zoom window 109b has moved to the right end of the right measurement region from the state of FIG. 12, the shapes of the zoom windows 109a and 109b change as shown in FIG. 15. For this reason, the zoom windows 109a and 109b do not overlap information, such as the object distance information 107. The first overlay information is displayed preferentially over the second overlay information, and the third overlay information is displayed preferentially over the first overlay information.

In the above case, if a predetermined region on the left image around the cursor position designated by the cursor position designating portion 41 protrudes from the left measurement region, the enlarged image generating portion 42 changes the shape of the predetermined region such that the predetermined region does not protrude from the left measurement region. In addition, if a predetermined region on the right image around the corresponding point of the cursor position calculated by the matching processing portion 44 protrudes from the right measurement region, the enlarged image generating portion 42 changes the shape of the predetermined region such that the predetermined region does not protrude from the right measurement region. The predetermined region is a region which is set as a region where the zoom window is displayed. The enlarged image generating portion 42 generates data of the enlarged image corresponding to the predetermined region the shape of which has been changed. In addition, the graphic processing portion 43 generates the graphic image signal obtained by changing the shape of the frame of the zoom window according to the change of the shape of the predetermined region. At this time, the frame of the zoom window shows a region where a measurement point can be input on the original image.

Figure 16:
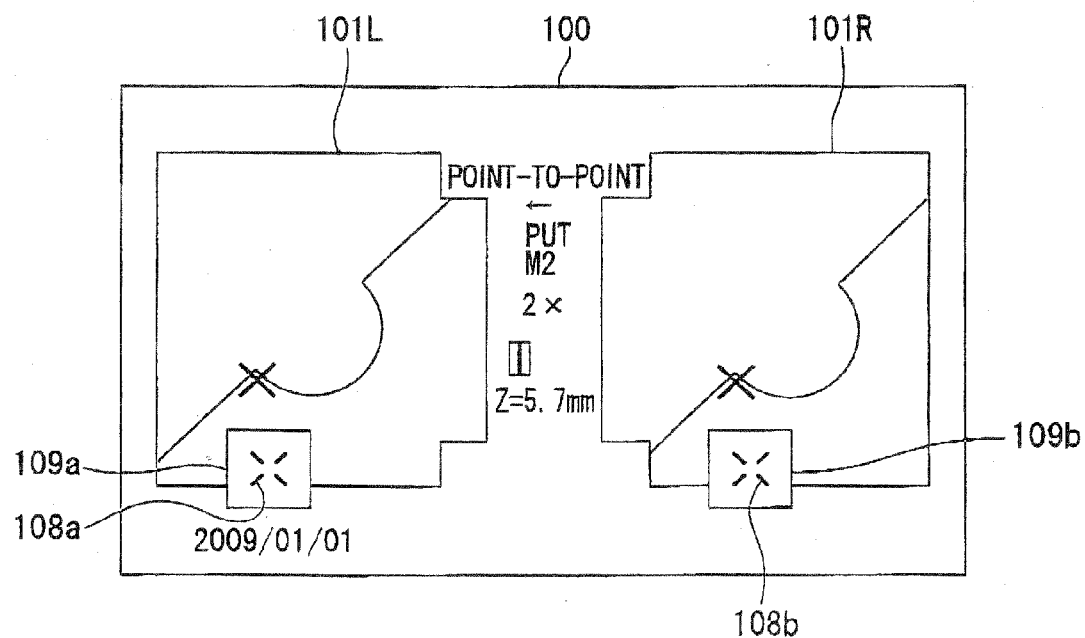
FIG. 16 is a view illustrating a display screen of the endoscope apparatus according to the embodiment of the invention.

The visibility of information, such as the measurement result, is maintained by displaying the information displayed outside the measurement region preferentially over the zoom window as described above. However, the shape of the zoom window may not be changed except for the case where the zoom window protrudes from the right end of the left measurement region or the case where the zoom window protrudes from the left end of the right measurement region. For example, it may be like FIG. 16. At this time, the zoom windows 109*a* and 109*b* may not be displayed when the cursors 108*a* and 108*b* are located outside the measurement region.

Figure 17:
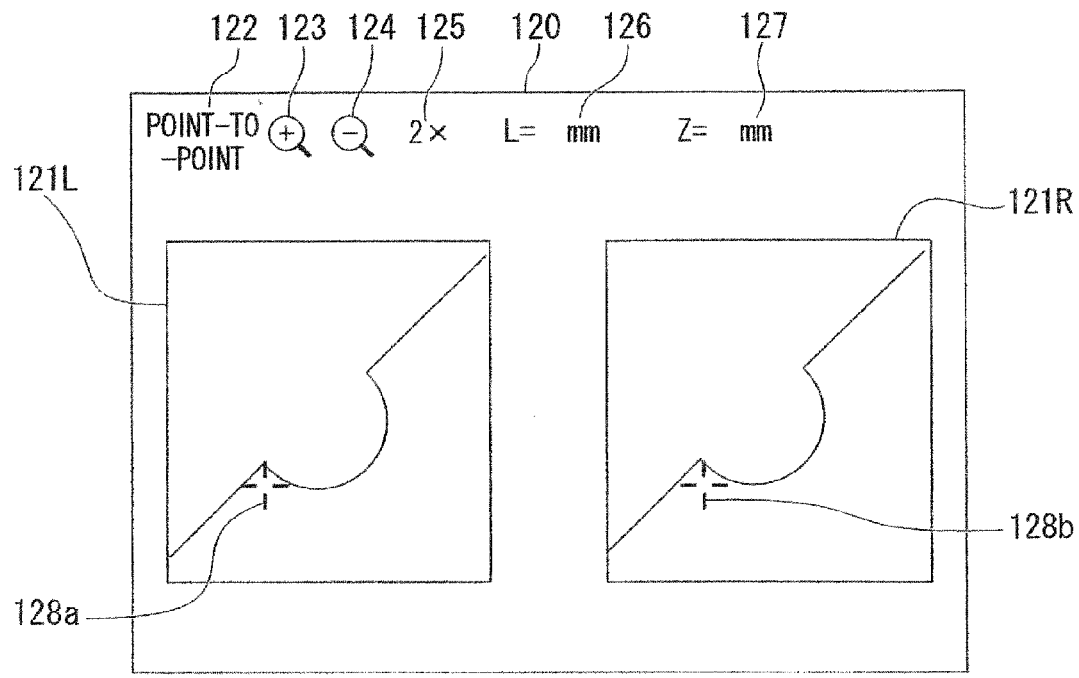
FIG. 17 is a view illustrating a display screen of the endoscope apparatus according to the embodiment of the invention.

Next, another example of the display screen of the present embodiment will be described. FIG. 17 shows a display screen 120 at the start of measurement. A pair of left and right images 121L and 121R with parallax, measurement operation information 122, an enlargement icon 123, a reduction icon 124, magnifying power information 125, measurement result information 126, object distance information 127, cursors 128*a* and 128*b*, and the like are displayed on the display screen 120.

The display screen 120 is configured to include a display region, which is provided in the I-shape in upper, lower, and middle parts of the screen of the monitor 4, and two rectangular display regions excluding the display region. The left image 121L is displayed in the left display region shown in the drawing, and the right image 121R is similarly displayed in the right display region. The measurement operation information 122, the enlargement icon 123, the reduction icon 124, the magnifying power information 125, the measurement result information 126, and the object distance information 127 are displayed in the upper part of the I-shaped display region. The cursor 128*a* is displayed so as to overlap the left image 121L, and the cursor 128*b* is displayed so as to overlap the right image 121R.

The measurement operation information 122 displays the kind of measurement operation, such as the distance between two points, the depth, the area, and the angle. In the present embodiment, it is shown that the measurement operation of the distance between two points is performed.

The enlargement icon 123 is for raising the magnification of an image displayed in the zoom window to be described later. The reduction icon 124 is for lowering the magnification of the image displayed in the zoom window. The magnifying power information 125 shows the magnifying power of the image displayed in the zoom window.

The measurement result information 126 displays the measurement result, such as point-to-point measurement. Before measurement processing is executed, the measurement result is not displayed on the measurement result information 126. The object distance information 127 shows the degree of the object distance. Before object distance calculating processing is executed, the object distance is not displayed on the object distance information 127.

The cursors 128*a* and 128*b* are used to input a measurement point on the display screen 120. The position of the cursor 128*a* is calculated according to the operation input from the cursor moving switch of the operating portion 6 by the cursor position designating portion 41. The position of the cursor 128*b* is calculated on the basis of the position of the cursor 128*a* by the matching processing portion 44. The cursor 128*a* changes to the arrow in the outside of the left measurement region where the left image 121L is displayed. The magnifying power of the image displayed in the zoom window can be changed by operating the enlargement icon 123 and the reduction icon 124 with this arrow.

Figure 18:
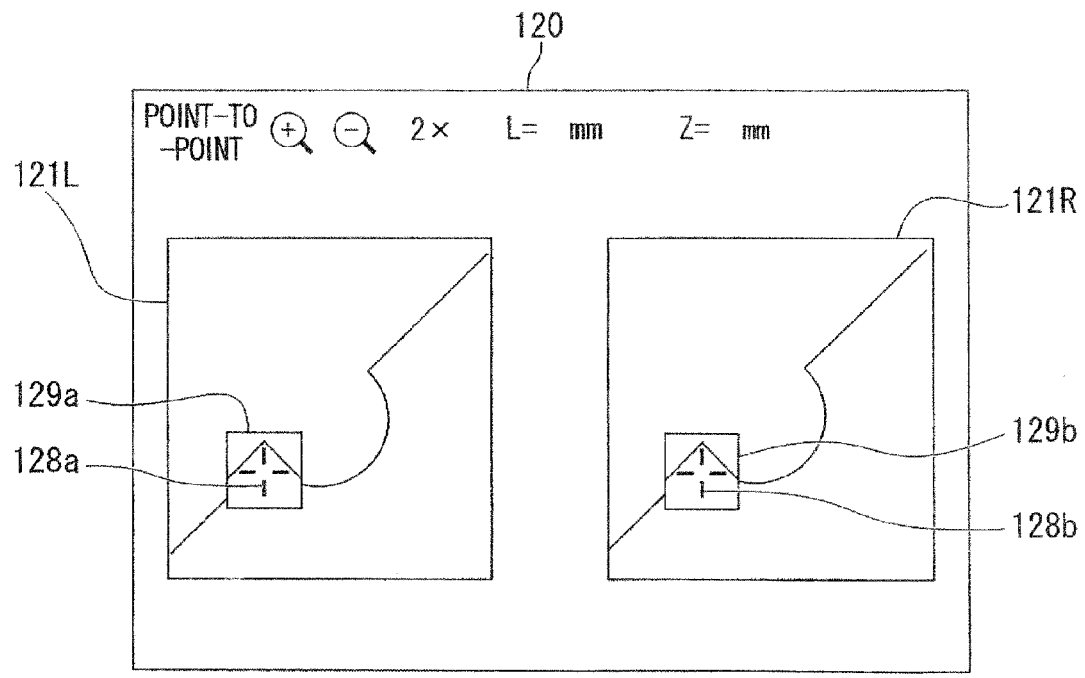
FIG. 18 is a view illustrating a display screen of the endoscope apparatus according to the embodiment of the invention.

When the zoom switch of the operating portion 6 is operated and display of the zoom window is instructed, zoom windows 129*a* and 129*b* are displayed as shown in FIG. 18. The zoom window 129*a* is displayed in the left image 121L, and the zoom window 129*b* is displayed in the right image 121R.

The cursor 128*a* and an enlarged image, which is obtained by enlarging an image within a predetermined range around the cursor 128*a* in the left image 121L, are displayed in the zoom window 129*a*. The cursor 128*b* and an enlarged image, which is obtained by enlarging an image within a predetermined range around the cursor 128*b* in the right image 121R, are displayed in the zoom window 129*b*. The size of each of the zoom windows 129*a* and 129*b* is 60×60 pixels, for example. When the magnifying power is 2×, the enlarged images obtained by enlarging, for example, images within the range of 30×30 pixels on the left and right images 121L and 121R are displayed in the zoom windows 129*a* and 129*b*, respectively.

The user can change the magnifying power of the enlarged image displayed in each of the zoom windows 129*a* and 129*b* by operating the enlargement icon 123 and the reduction icon 124. The magnifying power is increased when the enlargement icon 123 is operated in a state where the zoom windows 129*a* and 129*b* are displayed. In addition, the magnifying power is decreased when the reduction icon 124 is operated in a state where the zoom windows 129*a* and 129*b* are displayed. When the magnifying power is 1×, the zoom windows 129*a* and 129*b* are not displayed. In addition, the user can move the zoom windows 129*a* and 129*b* together with the cursors 128*a* and 128*b* by operating the cursor moving switch of the operating portion 6.

Figure 19:
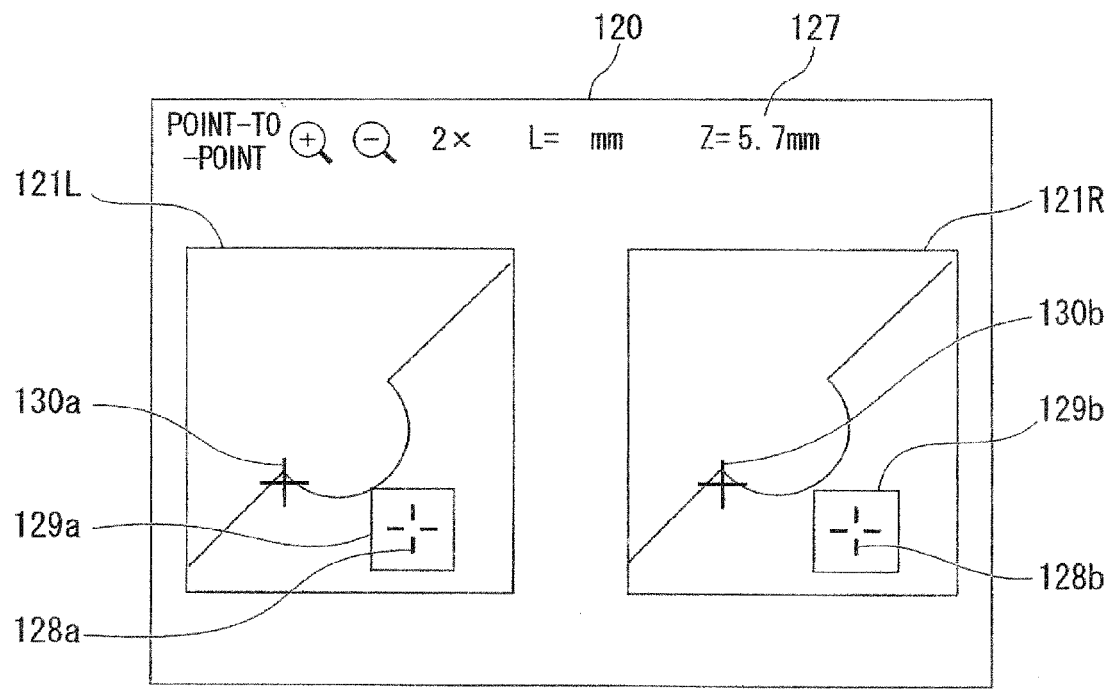
FIG. 19 is a view illustrating a display screen of the endoscope apparatus according to the embodiment of the invention.

Hereinafter, the transition of the display screen will be described using the point-to-point measurement as an example. When the user performs an operation of deciding a measurement point with the cursor moving switch of the operating portion 6 in a state where the cursor 128*a* is displayed at the desired position at which the user wants to set a first measurement point, the first measurement point is set at the position where the cursor 128*a* is displayed. FIG. 19 shows a state where the first measurement point is set. A first measurement point 130*a* is displayed on the left image 121L, and a corresponding point 130*b* corresponding to the measurement point 130*a* is displayed on the right image 121R. When the measurement point 130*a* is set the object distance is calculated and the object distance information 127 is displayed.

Then, when the user performs an operation of deciding a measurement point with the cursor moving switch of the operating portion 6 in a state where the cursor 128*a* is displayed at the desired position at which the user wants to set a second measurement point, the second measurement point is set at the position where the cursor 128*a* is displayed. When the second measurement point is set, the distance between the two points is calculated and displayed on the display screen 120 as a measurement result.

Figure 20:
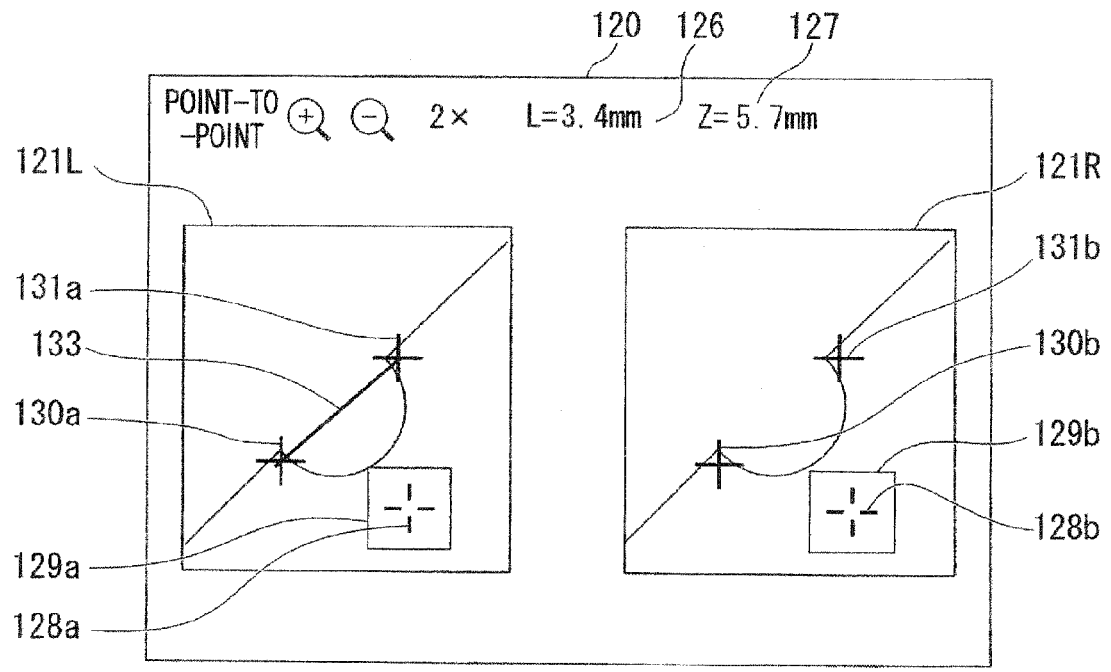
FIG. 20 is a view illustrating a display screen of the endoscope apparatus according to the embodiment of the invention.

FIG. 20 shows a state where the second measurement point is set. A second measurement point 131*a* is displayed on the left image 121L, and a corresponding point 131b corresponding to the measurement point 131a is displayed on the right image 121R. In addition, the measurement result information 126 indicating the result of the point-to-point measurement is displayed. In addition, a measurement line 133 which connects the measurement points 130a and 131a to each other is displayed. Moreover, in the point-to-point measurement of the present embodiment, even after the distance between two points has been calculated and the measurement result information 126 is displayed, the point-to-point measurement may be performed again by setting new first and second measurement points in a state where the measurement points 130a and 131a and the corresponding points 130b and 131b are displayed.

In the transition of the display screen shown in FIGS. 17 to 20, it is assumed that reducing the processing load of the endoscope apparatus 1 is not essential. Accordingly, the zoom windows 129a and 129b are displayed even during the movement of the cursors 128a and 128b. Moreover, even after the operation of deciding the measurement points 130a and 131a is performed, the zoom windows 129a and 129b are displayed.

Figure 8:
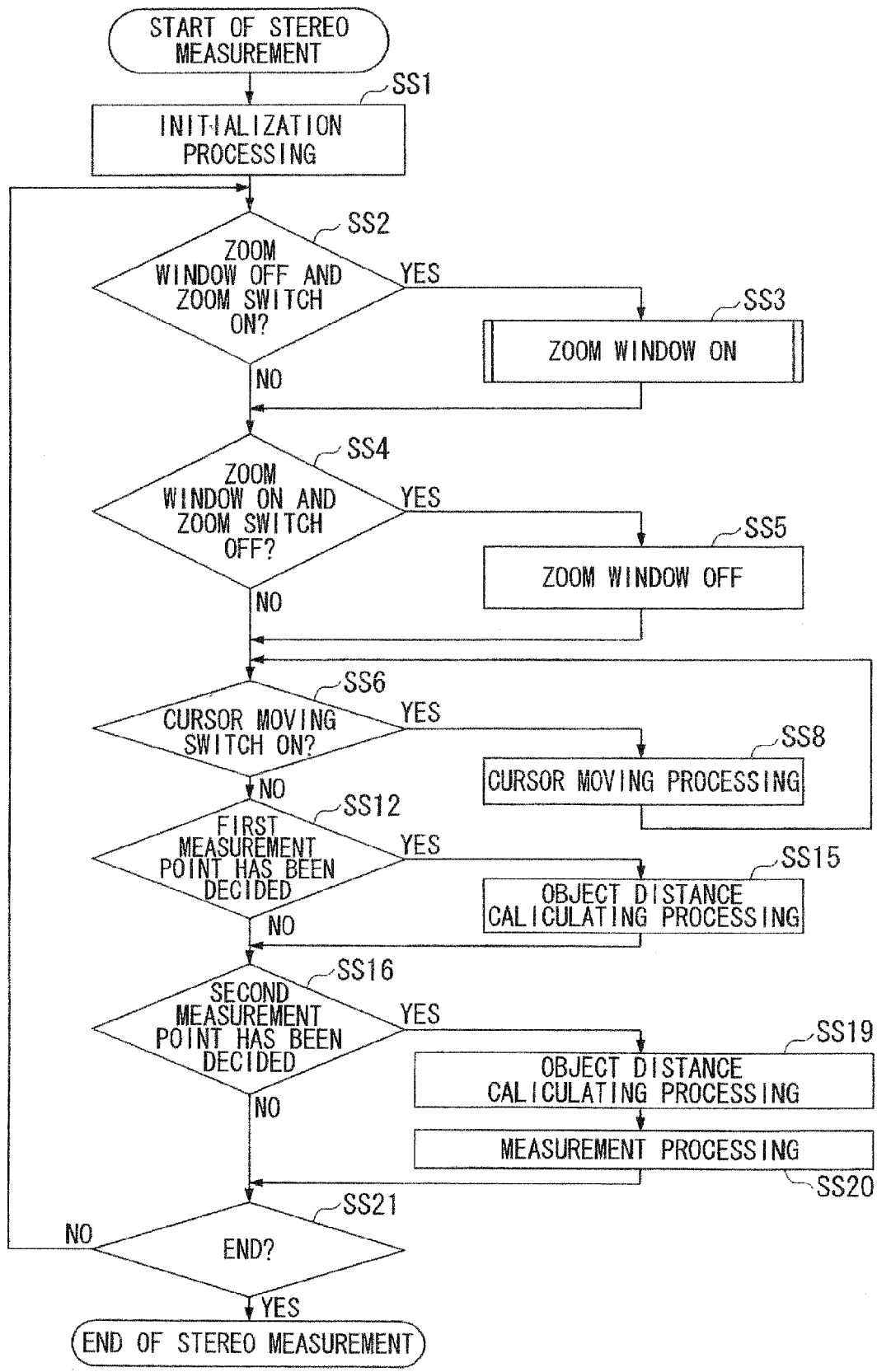
FIG. 8 is a flow chart illustrating the procedure of an operation of the endoscope apparatus according to the embodiment of the invention.

Next, details of step SS (stereo measurement) when displaying the display screen shown in FIGS. 17 to 20 will be described. The point-to-point measurement is exemplified below. FIG. 8 shows the procedure of stereo measurement. In FIG. 8, the same processing as the processing shown in FIGS. 5 and 6 is denoted by the same step number. The following explanation will be focused on a different part from the processing shown in FIGS. 5 and 6.

Processing of steps SS1 to SS5 is the same as the processing of steps SS1 to SS5 of FIG. 5. When the cursor moving switch is ON in step SS6, processing for moving the cursor is executed in step SS8 while the display/non-display state of the zoom window is not changed.

When the first measurement point is decided in step SS12, object distance calculating processing is executed in step SS15 to calculate the object distance while the display/non-display state of the zoom window is not changed. In addition, when the second measurement point is decided in step SS16, object distance calculating processing is executed in step SS19 to calculate the object distance while the display/non-display state of the zoom window is not changed. Then, measurement processing is executed in step SS20 to calculate the distance between the two points.

In the processing shown in FIG. 8, the measurement processing is executed after the second measurement point is decided. However, after the first measurement point is decided, the measurement processing may be executed before the second measurement point is decided. In addition, in the processing shown in FIG. 8, the object distance calculating processing is executed after the measurement point is decided. However, the object distance calculating processing may be always executed irrespective of whether or not the measurement point has been decided.

In addition, when it is determined that the matching degree between the measurement point on the left image and the corresponding point on the right image is low in step SS3, the zoom window on the right image may not be displayed.

Figure 21:
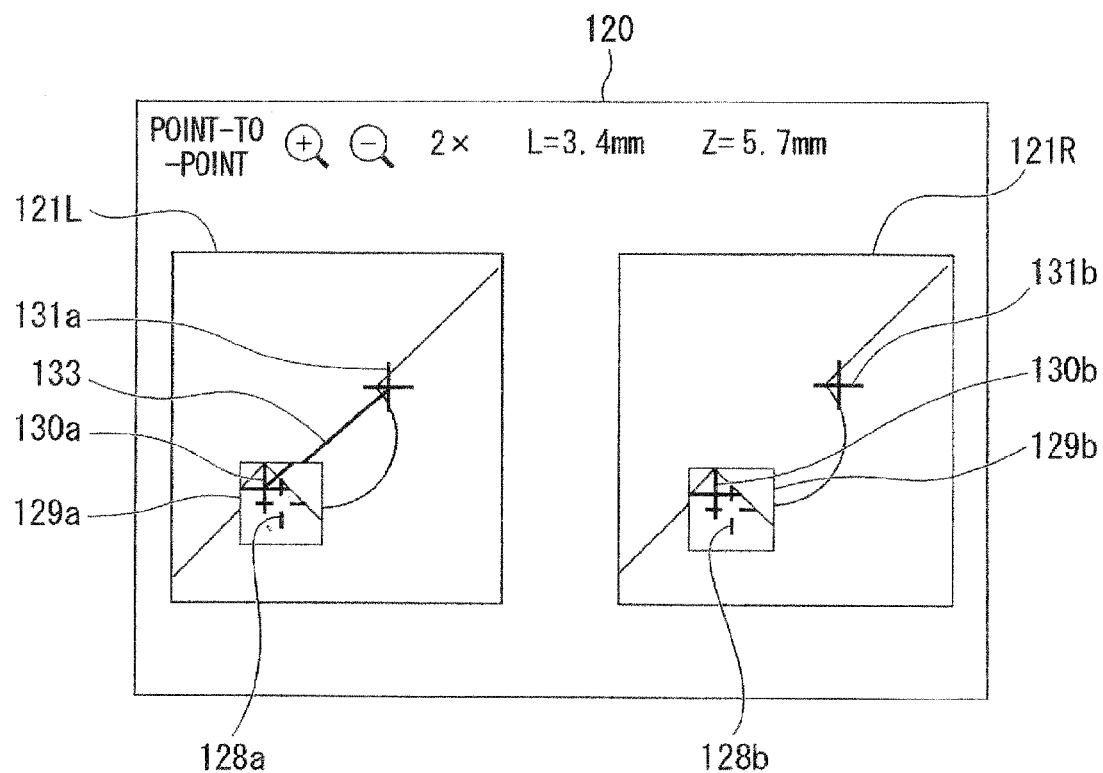
FIG. 21 is a view illustrating a display screen of the endoscope apparatus according to the embodiment of the invention.

Next, a control when the zoom window overlaps other parts in the display screen in transition of the display screen shown in FIGS. 17 to 20 will be described. Within the left measurement region where the left image is displayed and the right measurement region where the right image is displayed, the second overlay information is displayed so as to be included in the first overlay information when the first overlay information which is movable on the left image or the right image overlaps the second overlay information. Here, when the zoom window and the measurement point overlap each other, the measurement point is displayed in the zoom window. For example, when the zoom windows 129a and 129b have moved near the measurement point 130a and the corresponding point 130b from the state of FIG. 20, the measurement point 130a is displayed together with the cursor 128a in the zoom window 129a and the corresponding point 130b is displayed together with the cursor 128b in the zoom window 129b as shown in FIG. 21. In addition, the measurement line 133 is also displayed in the zoom window 129a. In addition, when the second overlay information, such as the measurement point 130a and the measurement line 133, is thus displayed in the zoom window which is the first overlay information, both the original image and the second overlay information may be enlarged and displayed in the zoom window, or only the original image may be enlarged and the second overlay information may be displayed in the zoom window with the original size.

By displaying the measurement point and the corresponding point in the zoom window together with the enlarged image as described above, the positions of the measurement point and corresponding point can be checked in the zoom window.

Figure 22:
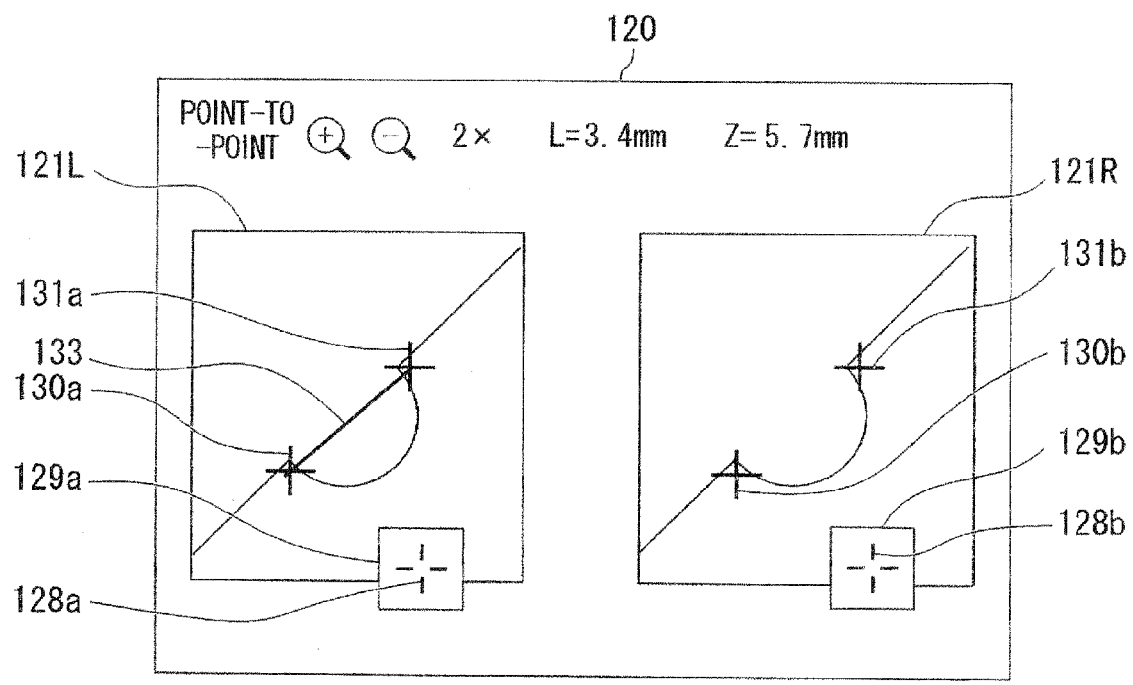
FIG. 22 is a view illustrating a display screen of the endoscope apparatus according to the embodiment of the invention.

In the outside of the left measurement region where the left image is displayed and the right measurement region where the right image is displayed, it is as follows. For example, when the zoom window 129a has moved to the lower end of the left measurement region and the zoom window 129b has moved to the lower end of the right measurement region from the state of FIG. 20, the zoom windows 129a and 129b are displayed outside the frame of the measurement region as shown in FIG. 22 if the position of the cursor 128a is within the left measurement region. In addition, if the position of the cursor 128a is outside the left measurement region, the zoom windows 129a and 129b are not displayed and the cursor 128a changes to the arrow. If this arrow moves to the inside of the left measurement region, the cursors 128a and 129b and the zoom windows 129a and 129b are displayed again.

In the above case, when the cursor position designated by the cursor position designating portion 41 is within the left measurement region, the enlarged image generating portion 42 generates data of left and right enlarged images obtained by enlarging images in predetermined regions on the left and right images as described above. The graphic processing portion 43 generates a graphic image signal such that the frame of the zoom window, the enlarged image, the measurement point, and the like are displayed so as to overlap on the frame of the measurement region.

In addition, the enlarged image generating portion 42 does not generate data of the enlarged image if the cursor position designated by the cursor position designating portion 41 is outside the left measurement region. The graphic processing portion 43 generates a graphic image signal including an arrow instead of the zoom window and the cursor.

On the display screen 120, information, such as a measurement result which is the third overlay information, is not displayed near the measurement regions where the left and right images are displayed. Accordingly, even if the zoom window is displayed across the measurement region, the visibility of the information, such as the measurement result, is not damaged. On the other hand, the visibility of the zoom window is maintained. The third overlay information is displayed such that the visibility is not damaged by the first overlay information.

As described above, in the present invention, the zoom window including the enlarged image around the cursor position is displayed together with the cursor at the cursor position designated by the cursor position designating portion 41, and the zoom window moves corresponding to the movement of the cursor. For this reason, problems in checking the enlarged image are reduced.

Moreover, as shown in FIG. 15, when the zoom window attempts to protrude from the measurement region, the visibility of information such as the measurement result displayed outside the measurement region can be maintained by changing the shape of the zoom window such that the zoom window is not displayed outside the measurement region.

In addition, as shown in FIG. 21, when the zoom window overlaps the measurement point and the corresponding point, the positions of the measurement point and corresponding point can be checked in the zoom window by displaying the measurement point and the corresponding point in the zoom window together with the enlarged images.

While preferred embodiments of the invention have been described and illustrated above, it should be understood that these are exemplary of the invention and are not to be considered as listing. Additions, omissions, substitutions, and other modifications can be made without departing from the spirit or scope of the present invention. Accordingly, the invention is not to be considered as being limited by the foregoing description and is only limited by the scope of the appended claims. For example, although the point-to-point measurement was described in the stereo measurement, the control regarding the display of the zoom window may also be applied for other measurements. Moreover in the above-described embodiments, the zoom window or the cursor was exemplified as the first overlay information, the measurement point, the corresponding point, or the measurement line was exemplified as the second overlay information, and the date and time information, the measurement operation information, the message information) the magnifying power information, the object distance information, or the measurement result information was exemplified as the third overlay information. However, examples of the overlay information are not limited to those described above and may be suitably changed according to the usage of the endoscope apparatus, the purpose of use of the endoscope apparatus, and the like. For example, when the measurement result information is displayed on the left image, the measurement result information may be considered as the second overlay information instead of the third overlay information.

According to the invention, since the enlarged image is displayed at the designated position together with the cursor and the displayed enlarged image moves corresponding to the movement of the cursor, problems in checking the enlarged image are reduced.

What is claimed is:

1. An endoscope apparatus comprising:
   an imaging portion that images a subject to generate image data;
   a designation portion that designates a position in an image based on the image data;
   an image processing portion that processes the image data such that an enlarged image obtained by enlarging an image in a second region including the designated position overlaps a first region including the designated position designated by the designation portion;
   a display portion that displays the enlarged image and the image of the subject based on the image data processed by the image processing portion and displays a cursor at the designated position on the enlarged image; and
   a measurement processing portion that performs measurement based on a measurement position indicated by the cursor by using the image data generated by the imaging portion,
   wherein the display portion displays the enlarged image such that the enlarged image moves according to movement of the cursor, and
   wherein the display portion does not display the enlarged image during the movement of the cursor.

2. The endoscope apparatus according to claim 1, wherein the display portion further displays the measurement position, and wherein the display portion displays the enlarged image such that the enlarged image moves with respect to the measurement position displayed on the display portion according to the designated position.

3. The endoscope apparatus according to claim 2, wherein when the designated position and the measurement position match each other, the display portion displays the enlarged image together with the measurement position such that the measurement position overlaps the enlarged image.

4. The endoscope apparatus according to claim 1, wherein the display portion further displays a result of the measurement performed by the measurement processing portion, and wherein the display portion displays the enlarged image such that the enlarged image moves with respect to the result of the measurement displayed on the display portion according to the designated position.

5. The endoscope apparatus according to claim 1, further comprising:
   a control portion that controls a shape of the enlarged image according to a relative position with respect to a predetermined range in the image based on the image data.

6. The endoscope apparatus according to claim 5, wherein the control portion controls the shape of the enlarged image such that the enlarged image is displayed only within the predetermined range.

7. A non-transitory computer readable medium having a program stored thereon for controlling an endoscope apparatus to perform functions comprising:
   imaging a subject using an imaging portion to generate image data;
   designating a position in an image based on the image data;
   processing the image data such that an enlarged image obtained by enlarging an image in a second region including the designated position overlaps a first region including the designated position that has been designated;
   displaying the enlarged image and the image of the subject based on the processed image data and displaying a cursor at the designated position on the enlarged image; and
   performing measurement based on a measurement position indicated by the cursor by using the image data generated by the imaging portion,
   wherein the enlarged image is displayed so as to move according to movement of the cursor, and
   wherein the enlarged image is not displayed during the movement of the cursor.

8. A method of controlling an endoscope apparatus to perform functions comprising:
   imaging a subject using an imaging portion to generate image data;
   designating a position in an image based on the image data;
   processing the image data such that an enlarged image obtained by enlarging an image in a second region including the designated position overlaps a first region including the designated position that has been designated;

displaying on a display portion the enlarged image and the image of the subject based on the processed image data and displaying on the display portion a cursor at the designated position on the enlarged image; and performing measurement based on a measurement position indicated by the cursor by using the image data generated by the imaging portion, wherein the enlarged image is displayed on the display portion so as to move according to movement of the cursor, and wherein the enlarged image is not displayed on the display portion during the movement of the cursor.

* * * * *